(12) United States Patent
Kawakami et al.

(10) Patent No.: US 7,473,415 B2
(45) Date of Patent: Jan. 6, 2009

(54) NEAR INFRARED FLUORESCENT CONTRAST AGENT AND METHOD FOR FLUORESCENCE IMAGING

(75) Inventors: Masayuki Kawakami, Minami-ashigara (JP); Hiroshi Kitaguchi, Minami-ashigara (JP); Kai Licha, Falkensee (DE); Christin Perlitz, Berlin (DE); Hiroaki Eguchi, Kawanishi (JP); Natsuko Tsuda, Nishinomiya (JP); Kazuhiro Aikawa, Minami-ashigara (JP)

(73) Assignees: Fuji Photo Film Co., Ltd., Kanagawa (JP); Schering Aktiengesellschaft, Berlin (DE)

( * ) Notice: Subject to any disclaimer, the term of this patent is extended or adjusted under 35 U.S.C. 154(b) by 191 days.

(21) Appl. No.: 10/506,819

(22) PCT Filed: Mar. 7, 2003

(86) PCT No.: PCT/EP03/02358

§ 371 (c)(1),
(2), (4) Date: Apr. 19, 2005

(87) PCT Pub. No.: WO03/074091

PCT Pub. Date: Sep. 12, 2003

(65) Prior Publication Data

US 2005/0226815 A1   Oct. 13, 2005

(30) Foreign Application Priority Data

Mar. 7, 2002   (JP)   .............................. 2002-109794

(51) Int. Cl.
*A61K 51/00*   (2006.01)
*A61M 36/14*   (2006.01)

(52) U.S. Cl. .................. 424/9.6; 424/9.1; 424/1.11; 424/1.65; 548/400

(58) Field of Classification Search ................ 424/1.11, 424/1.65, 9.1, 9.6; 548/400, 455
See application file for complete search history.

(56) References Cited

U.S. PATENT DOCUMENTS

| 6,319,488 | B1 | 11/2001 | Licha et al. |
| 6,395,257 | B1 * | 5/2002 | Achilefu et al. .............. 424/9.6 |
| 6,939,975 | B2 * | 9/2005 | Kawakami et al. .......... 548/455 |
| 2002/0064782 | A1 | 5/2002 | Shinoki et al. |

FOREIGN PATENT DOCUMENTS

| DE | 199 57 007 | 5/2001 |
| EP | 1 152 008 | 11/2001 |
| EP | 1 308 480 | 5/2003 |
| WO | WO 97 13490 | 4/1997 |
| WO | WO 01/53292 | 7/2001 |
| WO | WO 02 12398 | 2/2002 |
| WO | WO 02 32860 | 4/2002 |

* cited by examiner

*Primary Examiner*—D. L Jones
(74) *Attorney, Agent, or Firm*—Millen, White, Zelano & Branigan, P.C.

(57) ABSTRACT

A near infrared fluorescent contrast agent which is excellent in permeability in a living tissue and enables specific imaging of tumor and/or blood vessel, comprising a compound represented by formula (I) or a pharmaceutically acceptable salt thereof, wherein $R^1$, $R^2$, $R^7$, and $R^8$ represent a $C_1$-$C_{10}$ alkyl group or the like; $R^3$, $R^4$, $R^5$, $R^6$, $R^9$, $R^{10}$, $R^{11}$, and $R^{12}$ represent a hydrogen atom, a $C_1$-$C_6$ alkyl group, an aryl group or the like; $X^1$ and $X^2$ represent a $C_1$-$C_{15}$ alkyl group or an aryl group and $X^1$ and $X^2$ in total have 0 to 4 carboxyl groups; $m^1$, $m^2$, and $m^3$ represents 0 or 1; $L^1$ to $L^7$ independently represent a methine group; M represents a hydrogen atom, a metal, or a quaternary ammonium salt; and n represents an integer of 1 to 7 necessary for neutralizing charge.

17 Claims, 8 Drawing Sheets

No.:8, mouse 17, 0 min., File 10SLi7

No.:8, mouse 17, 1 min., File 10SLi12

No.:8, mouse 17, 10 min., File 10SLi17

No.:8, mouse 17, 30 min., File 10SLi30

No.:8, mouse 17, 1h, File 10SLi43

No.:8, mouse 17, 4h, File 10SLi53

No.:8, mouse 17, 24h, File 11SLi2

NEAR INFRARED FLUORESCENT CONTRAST AGENT AND METHOD FOR FLUORESCENCE IMAGING

TECHNICAL FIELD

The present invention relates to a near infrared fluorescent contrast agent, and a method of fluorescence imaging using said near infrared fluorescent contract agent.

BACKGROUND ART

In treating disease, it is important to detect morphological and functional changes caused by the disease in the living body at an early stage of the disease. Especially for treatment of a cancer, to know the site and size of the tumor beforehand is an extremely important means to determine strategies and protocols for future treatment. Methods so far applied include biopsy by puncture and the like, as well as imaging diagnosis such as X-ray imaging, MRI, ultrasound imaging and the like. Biopsy is an effective means for definitive diagnosis, however, it places great burden on a patient to be diagnosed, and also is not suitable for tracing changes with time in lesions. X-ray imaging and MRI inevitably cause exposure of a patient to be diagnosed with irradiation or electromagnetic wave. In addition, conventional imaging diagnoses as mentioned above require complicated operation and a prolonged time for measurement and diagnosis. A large size of an apparatus also makes it difficult to apply these methods during surgical operation.

One of reported image diagnoses includes fluorescence imaging (Lipspn R. L. et al., J. Natl. Cancer Inst., 26, 1-11 (1961)). This method employs a substance as a contrast agent that emits fluorescence upon exposure to an excitation light having a specific wavelength. The method comprises the step of exposing a body with an excitation light from outside the body and then detecting fluorescence emitted from the fluorescent contrast agent in vivo.

An example of the fluorescent contrast agent include, for example, a porphyrin compound that accumulates in tumor and is used for photodynamic therapy (PDT), e.g., haematoporphyrin. Other examples include photophyrin and benzoporphyrin (see, Lipspn R. L. et al., supra, Meng T. S. et al., SPIE, 1641, 90-98 (1992), WO84/04665 an the like). However, these compounds have phototoxicity since they are originally used for PDT (PDT requires such property), and accordingly, these compounds are not desirable as diagnostic agents.

Retinal circulatory microangiography using a known fluorescent dye, such as fluorescein, fluorescamine, and riboflabin, has been known (U.S. Pat. No. 4,945,239). However, these fluorescent dyes emit fluorescence in a region of a visible light of 400-600 nm which only achieves low transmission through living tissue, and consequently, detection of a lesion in a deeper part of a body is almost impossible.

Cyanine compounds including indocyanine green (hereinafter abbreviated as "ICG"), which are used to determine liver function and cardiac output, have been also reported to be useful as fluorescent contrast agents (Haglund M. M. et al., Neurosurgery, 35, 930 (1994), Li, X. et al., SPIE, 2389, 789-797 (1995)). Cyanine compounds have absorbance in a near infrared light region (700 to 1300 nm).

Near infrared light has a high transmission property through living tissues and can pass through the skull of about 10 cm, and from these reasons, said light has been focused recently in the field of clinical medicine. For example, the optical CT technique (a CT technique using optical transmission of a medium) has become focused as a new technology in the clinical field, because near infrared light can pass through a living body and, oxygen concentration and circulation in vivo can be detected by using a light within this region.

The cyanine compound emits fluorescence in the near infrared region, a light of which region has excellent permeability in living tissues as explained above, and accordingly a use as a fluorescent contrast agent has been proposed. Various cyanine compounds have been developed in recent years, and approaches for use as fluorescent contrast agents have been made (WO96/17628, WP97/13490 and the like). However, an agent having a satisfactory distinguishing ability of a lesion from normal tissues, i.e., an agent having a satisfactory selectively to a target site to be imaged, has not yet been available.

DISCLOSURE OF THE INVENTION

An object of the present invention is to provide a fluorescent contrast agent which emits fluorescence in the near infrared region that is excellent in permeability in a living tissue, and enables specific imaging of tumor and/or blood vessel. Another object of the present invention is to provide a method of fluorescence imaging using said near infrared fluorescent contract agent.

The inventors of the present invention conducted various studies to achieve the foregoing objects. As a result, by introducing carboxylic acid or an aryl group to cyanine dyes, they succeeded in providing a fluorescent contrast agent having high tumor selectivity. They also succeeded in establishing a method for fluorescence imaging by using said contrast agent. The present invention was achieved on the basis of the above findings.

The present invention thus provides a near infrared fluorescent contrast agent comprising a compound represented by the following formula [I] or a pharmaceutically acceptable salt thereof:

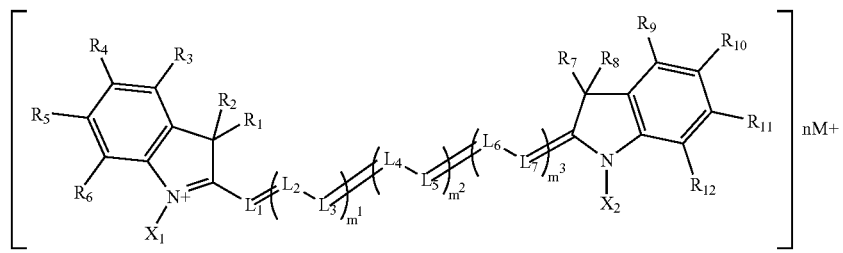

wherein $R^1$, $R^2$, $R^7$, and $R^8$ independently represent a substituted or unsubstituted $C_1$-$C_{10}$ alkyl group or a substituted or unsubstituted aryl group, and $R^1$ and $R^2$ and/or $R^7$ and $R^8$ may bind to each other to form a ring; $R^3$, $R^4$, $R^5$, $R^6$, $R^9$, $R^{10}$, $R^{11}$, and $R^{12}$ independently represent a hydrogen atom, a substituted or unsubstituted $C_1$-$C_6$ alkyl group, a substituted or unsubstituted aryl group, a substituted or unsubstituted heteroaryl group, a halogen atom, cyano group, carboxyl group, or sulfo group, and $R^3$, $R^{4,}R^5$, $R^6$, $R^9$, $R^{10}$, $R^{11}$, and $R^{12}$ may bind to each other to form a ring; $X^1$ and $X^2$ independently represent a substituted or unsubstituted $C_1$-$C_{15}$ alkyl group or a substituted or unsubstituted aryl group and $X^1$ and $X^2$ in total have 0 to 4 carboxyl groups, provided that when the number of the carboxyl group is 0 or 1, each of $X^1$ and $X^2$ is a $C_1$-$C_5$ carboxyalkyl group or a sulfoalkyl group and at least one of $R^3$, $R^4$, $R^5$, $R^6$, $R^9$, $R^{10}$, $R^{11}$, and $R^{12}$ represents a substituted or unsubstituted aryl group or a substituted or unsubstituted heteroaryl group; $m^1$ represents 0 or 1; $m^2$ represents 0 or 1; $m^3$ represents 0 or 1; $L^1$, $L^2$, $L^3$, $L^4$, $L^5$, $L^6$, and $L^7$ independently represent a substituted or unsubstituted methine group, provided that when two or more of the methine groups have substituents, the substituent may bind to each other to form a ring, provided that when each of $X^1$ and $X^2$ has one carboxyl group, each of $X^1$ and $X^2$ is carboxyl group-substituted hydrocarbon group and at least: one of the methine groups represented by $L^1$, $L^2$, $L^3$, $L^4$, $L^5$, $L^6$, and $L^7$ is a substituted methine group and $R^4$ and $R^{10}$ represent a sulfo group; M represents a hydrogen atom, a metal, or a quaternary ammonium salt; and n represents an integer of 1 to 7 necessary for neutralizing charge.

According to a preferred embodiment of the above invention, each of $m^1$, $m^2$, and $m^3$ is simultaneously 1, and $X^1$ is a group represented by the following formula (i):

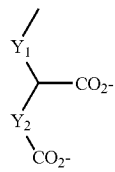

wherein $Y^1$ and $Y^2$ independently represent a substituted or unsubstituted divalent linking group.

According to a more preferred embodiment, $X^1$ and $X^2$ independently represent a group represented by the following formula (i):

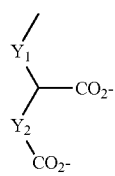

wherein $Y^1$ and $Y^2$ independently represent a substituted or unsubstituted a divalent bond.

According to further preferred embodiment, at least one of $R^3$, $R^4$, $R^5$, $R^6$, $R^9$, $R^{10}$, $R^{11}$, and $R^{12}$ is a substituted or unsubstituted aryl group or a substituted or unsubstituted heteroaryl group, and according to still further preferred embodiment, at least one of $R^4$, $R^5$, $R^{10}$, and $R^{11}$ is a substituted or unsubstituted aryl group or a substituted or unsubstituted heteroaryl group; and each of $X^1$ and $X^2$ is independently a $C_1$-$C_5$ carboxyalkyl group or a sulfoalkyl group.

According to another preferred embodiment, $X^1$ and $X^2$ independently represent a group represented by the following formula:

wherein $Y^3$ represents a $C_1$-$C_{10}$ hydrocarbon group and at least one of the methine groups represented by $L^1$, $L^2$, $L^3$, $L^4$, $L^5$, $L^6$, and $L^7$ is a substituted methine group and each of $R^4$ and $R^{10}$ is a sulfo group.

Preferably, the number of sulfo group in a molecule is two or less.

According to further preferred embodiment, $Y_1$ represents —$(CH_2)_p$CONH— wherein p represents an integer of 1 to 4 and $Y_2$ represents —$(CH_2)$— or $(CH_2)_2$—.

The aforementioned near infrared fluorescent contrast agent may preferably be used for tumor imaging or angiography.

From another aspect, provided is a method of fluorescence imaging which comprises the steps of introducing the aforementioned near infrared fluorescent contrast agent into a living body, exposing said body to an excitation light, and detecting near infrared fluorescence from the contrast agent.

BEST MODE FOR CARRYING OUT THE INVENTION

Figure 1:
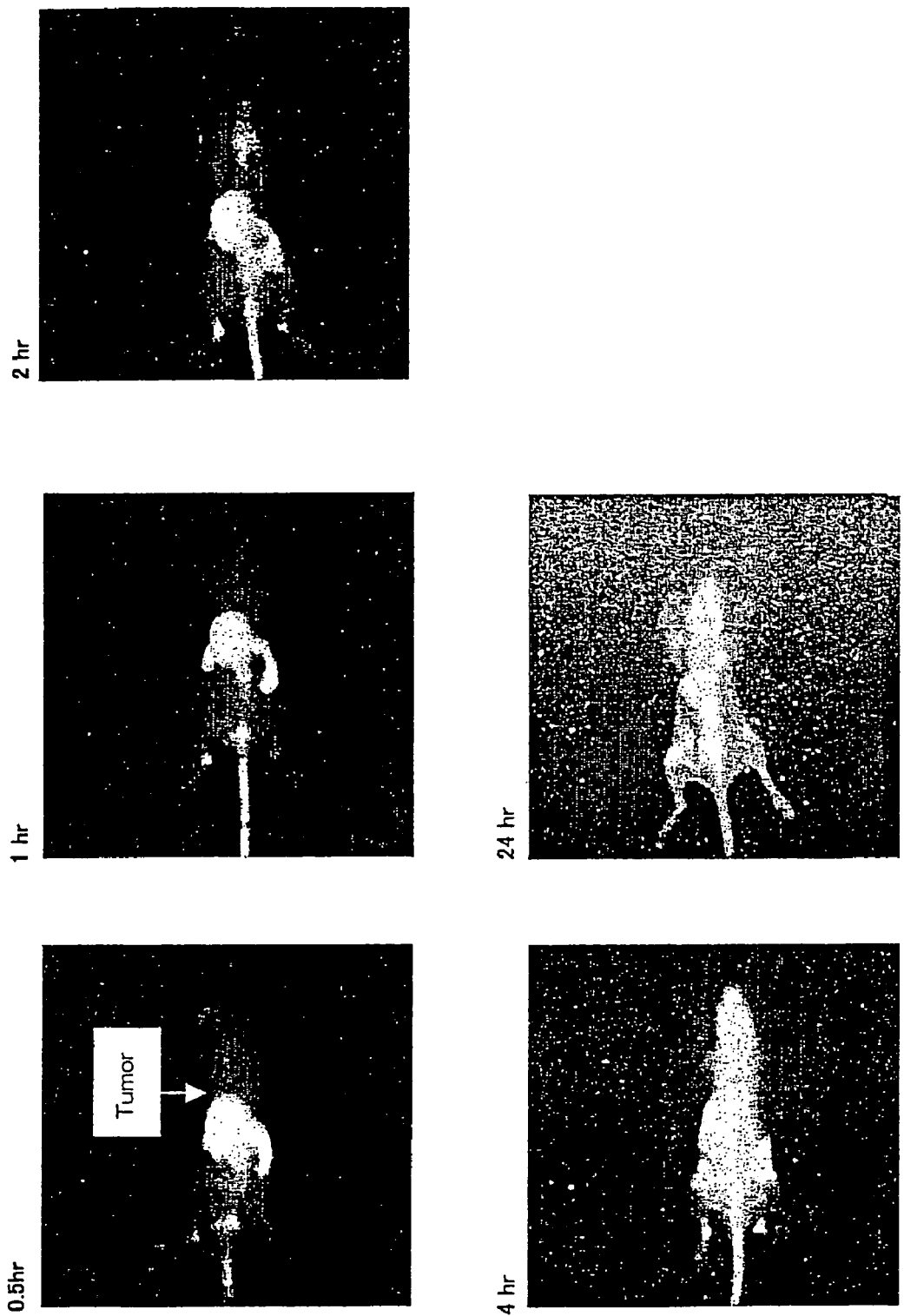
FIG. 1 is a photograph showing the results of fluorescence imaging at given times after the administration of Compound 2 of the present invention.

The $C_1$-$C_{10}$ alkyl group represented by $R^1$, $R^2$, $R^7$, and $R^8$ may be linear, branched, cyclic, or a combination thereof (an alkyl group and an alkyl moiety of a functional group containing the alkyl moiety have the same meaning in the specification unless otherwise specifically mentioned). As the unsubstituted alkyl group, for example, methyl group, ethyl group, propyl group, butyl group, and hexyl group can be used. The number, kind, or position of substituents on the substituted alkyl group are not particularly limited. As the substituted alkyl, for example, sulfoalkyl group, carboxylalkyl group, hydroxyalkyl group, alkoxyalkyl group, aminoalkyl group, halogenated alkyl group, cyanoalkyl group, aryl-substituted alkyl group, heteroaryl-substituted alkyl group and the like can be used.

The aryl group represented by $R^1$, $R^2$; $R^7$, and $R^8$ may be either a monocyclic ring or a condensed ring, for example, a $C_6$-$C_{14}$ aryl group, preferably $C_6$-$C_{10}$ aryl group can be used (an aryl group and an aryl moiety of a functional group containing the aryl moiety have the same meaning unless otherwise specifically mentioned). As the aryl group, preferably phenyl group or naphthyl group, more preferably phenyl group may used. As the substituted aryl group, sulfophenyl group, hydroxyphenyl group, aminophenyl group can be used.

Further, $R^1$ and $R^2$, $R^7$ and $R^8$ may bind to each other to form a ring. Examples of the ring formed include, for example, cyclopentyl ring, cyclohexyl ring and the like. $R^1$, $R^2$, $R^7$, and $R^8$ are preferably methyl group or ethyl group, more preferably methyl group.

$R^3$, $R^4$, $R^5$, $R^6$, $R^9$, $R^{10}$, $R^{11}$, and $R^{12}$ independently represent a hydrogen atom, a substituted or unsubstituted $C_1$-$C_6$ alkyl group, a substituted or unsubstituted aryl group, a substituted or unsubstituted heteroaryl group, a halogen atom, cyano group, carboxyl group, or sulfo group, and two adjacent groups selected from the group consisting of $R^3$, $R^4$, $R^5$, and $R^6$ or those selected from the group consisting of $R^9$, $R^{10}$, $R^{11}$, and $R^{12}$ may independently bind to each other to form a ring. The ring formed may be saturated or unsaturated, and may be a hydrocarbon ring or a heterocyclic ring. For example, $R^3$ and $R^4$, $R^4$ and $R^5$, $R^5$ and $R^6$, $R^9$ and $R^{10}$, $R^{10}$ and $R^{11}$, or $R^{11}$ and $R^{12}$ can bind to each other to form a benzene ring or an aromatic heterocyclic ring such as pyridine ring. Preferred examples include a benzene ring formed by binding of $R^3$ and $R^4$, or $R^9$ and $R^{10}$.

As the aryl group represented by $R^3$, $R^4$, $R^5$, $R^6$, $R^9$, $R^{10}$, $R^{11}$, and $R^{12}$, for example, phenyl group or naphthyl group can be used, as the heteroaryl group, for example, thienyl group, benzothienyl group, furyl group, benzofuryl group, pyrrolyl group, imidazolyl group, or quinolyl group can be used. One to four optional substituents may be present on the aryl group and the heteroaryl group. The position of the substituents is not limited, and when two or more substituents are present, they may be same or different. As such substituents, for example, hydroxyl group, a halogen atom such as fluorine atom, chlorine atom, bromine atom, and iodine atom; a $C_1$-$C_6$ alkyl group such as methyl group, ethyl group, n-propyl group, isopropyl group, n-butyl group, sec-butyl group, tert-butyl group; $C_1$-$C_6$ halogenated alkyl group such as trifluoromethyl group; a $C_1$-$C_6$ alkoxyl group such as methoxy group, ethoxy group, n-propoxy group, isopropoxy group, n-butoxy group, sec-butoxy group, tert-butoxy group; a $C_1$-$C_6$ alkylenedioxy group such as methylenedioxy group, ethylenedioxy group; carboxyl group; a $C_1$-$C_6$ alkoxycarbonyl group; an unsubstituted amino group; a $C_1$-$C_6$ alkyl-substituted amino group such as methylamino group, dimethylamino group, ethylamino group; a sulfo group; or a cyano group and the like can be used.

$X^1$ and $X^2$ independently represent a substituted or unsubstituted $C_1$-$C_{15}$ alkyl group or a substituted or unsubstituted aryl group, and $X^1$ and $X^2$ have one to four carboxyl groups in total of $X^1$ and $X^2$. As the unsubstituted alkyl represented by $X^1$ and $X^2$, for example, methyl group, ethyl group, propyl group, butyl group, isobutyl group, sec-butyl group, tert-butyl group, pentyl group, isopentyl group, neopentyl group, tert-pentyl group, 2-methylpropyl group, or 1,1-dimethylpropyl group can be used. The alkyl group may be linear, branched, cyclic, or a combination thereof, and a linear or branched alkyl group is preferred.

As the substituted alkyl group represented by $X^1$ and $X^2$, for example, a sulfoalkyl group (such as 2-sulfoethyl group, 3-sulfopropyl group, 3-methyl-3-sulfopropyl group, 4-sulfobutyl group and the like), a carboxyalkyl group (such as 1-carboxymethyl group, 2-carboxyethyl group, 3-carboxypropyl group, 4-carboxybutyl group and the like), a hydroxyalkyl group, an alkoxyalkyl group, an aminoalkyl group, a halogenated alkyl group, a cyanoalkyl group, a heteroaryl-substituted alkyl group, an aryl group, or a heteroaryl group can be used. The alkyl moiety of these groups is the same as those defined in the above-mentioned unsubstituted alkyl group. As the substituted or unsubstituted aryl group represented by $R^1$, $R^2$, $R^7$, and $R^8$, phenyl group, sulfophenyl group, hydroxyphenyl group, or aminophenyl group can be used.

When the number of carboxyl group of $X^1$ and $X^2$ is 0 or 1, a $C_1$-$C_5$ carboxyalkyl group or a sulfoalkyl group can be used as the $X^1$ and $X^2$.

As the divalent liking group represented by $Y^1$ and $Y^2$, for example, a substituted or unsubstituted $C_1$-$C_6$ alkylene group such as methylene group, ethylene group, n-butylene group, methylpropylene group, or phenylene group can be used. As another example, a linking group represented by the following formula can be used:

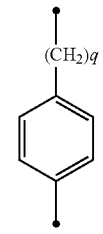

wherein q represents an integer of 1 to 4, and the symbol "." represents a bonding position. These hydrocarbon groups may have substituents and may contain one or more hetero atoms. For example, they may contain an ether bond, a thioether bond, a disulfide bond, an amide bond, an ester bond, a sulfonamide bond, or a sulfoester bond.

As the divalent linking group represented by $Y^1$ and $Y^2$, for examples a bond represented by the following formula can also be used:

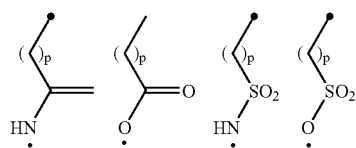

-continued

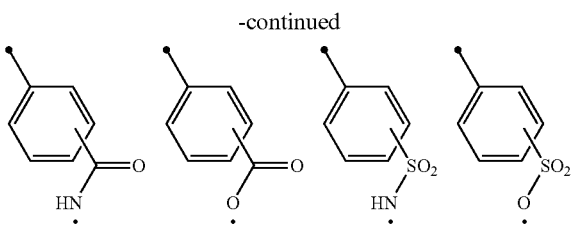

wherein p represents an integer of 1 to 4, and the symbol "." represents a bonding position. An preferred example of $Y^1$ include a linking group represented by the following formula:

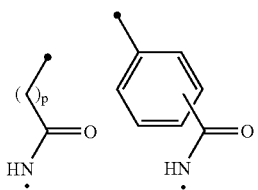

wherein p represents an integer of 1 to 4. Most preferably, $Y^1$ is —$(CH_2)_p$—CO—NH— (wherein p represents an integer of 1 to 4). Preferred examples of $Y^2$ include methylene group or ethylene group.

$L^1$, $L^2$, $L^3$, $L^4$, $L^5$, $L^6$, and $L^7$ independently represent a substituted or unsubstituted methine group, wherein $m^1$, $m^2$, and $m^3$ independently represent 0 or 1. It is preferred that each of $m^1$, $m^2$, and $m^3$ is simultaneously 1. Examples of the substituent on the methine group include a substituted or unsubstituted alkyl group, a halogen atom, a substituted or unsubstituted aryl group, or a lower alkoxy group and the like. An specific examples of the substituted aryl group includes 4-chlorophenyl group and the like. The lower alkoxy group may preferably be a $C_1$-$C_6$ alkoxy group which may be linear or branched. Specific examples include methoxy group, ethoxy group, propoxy group, butoxy group, tert-butoxy group, pentyloxy group and the like, and methoxy group or ethoxy group is preferred. As the substituent of the methine group, methyl group or phenyl group can preferably be used.

When the methine groups selected from $L^1$, $L^2$, $L^3$, $L^4$, $L^5$, $L^6$, and $L^7$ are substituted, the substituents on the methine groups may bind to each other to form a ring. Preferably, the substituents on the methine groups may bind to form a ring containing three successive methine group selected from the group consisting of $L^1$, $L^2$, $L^3$, $L^4$, $L^5$, $L^6$, and $L^7$. As an example wherein the substituents on the methine groups bind to each other to form a ring containing three successive methine group selected from the group of $L^1$, $L^2$, $L^3$, $L^4$, $L^5$, $L^6$, and $L^7$ include, for example, a compound wherein 4,4-dimethylcyclohexene ring is formed to contain $L^3$, $L^4$, and $L^5$. A particularly preferred example of a partial structure in which a conjugated methine chain formed by methine groups selected from the group of $L^1$, $L^2$, $L^3$, $L^4$, $L^5$, $L^6$, and $L^7$ contains a ring includes a group represented by the following general formula (a):

wherein Z represents a nonmetallic atom group necessary for forming a 5- or 6-membered ring, and A represents a hydrogen atom or a monovalent group.

Examples of the nonmetallic atom group necessary for forming a 5- to 10-membered ring represented by Z include, for example, a carbon atom, a nitrogen atom, an oxygen atom, a hydrogen atom, a sulfur atom, a halogen atom (fluorine atom, chlorine atom, bromine atom, iodine atom) and the like. Examples of the 5- or 6-membered ring in the partial structure represented by the general formula (a) include, for example, cyclopentene ring, cyclohexene ring, and 4,4-dimethylhexene ring, and cyclopentene ring or cyclohexene ring is preferred.

Examples of the monovalent group represented by A include, for example, a substituted or unsubstituted alkyl group, a substituted or unsubstituted aryl group, a substituted or unsubstituted aralkyl group, a substituted or unsubstituted lower alkoxy group, a substituted or unsubstituted amino group, a substituted or unsubstituted alkylcarbonyloxy group (such as acetoxy group), a substituted or unsubstituted alkylthio group, a substituted or unsubstituted arylthio group, cyano group, nitro group, a halogen atom and the like.

Specific examples of the aralkyl group represented by A include benzyl group, 2-phenylethyl group, 3-phenylpropyl and the like. Examples of the substituent of the aralkyl group include, for example, sulfo group, carboxyl group, hydroxyl group, a substituted or unsubstituted alkyl, group, an alkoxy group, a halogen atom and the like. Specific examples of the substituted amino group represented by A include, for example, an alkylamino group (such as methylamino group, ethylamino group and the like), a dialkylamino group (such as dimethyl amino group, diethylamino group and the like), phenylamino group, diphenylamino group, methylphenylamino group, a cyclic amino group (such as morpholino group, imidazolidino group, ethoxycarbonylpiperadino group and the like). When the substituted amino group has a further substituent, sulfo group, carboxyl group and the like can be used as the substituent. Specific examples of the arylthio group represented by A include phenylthio group, naphthylthio group and the like, and examples of a substituent of the arylthio group include sulfo group, carboxyl group and the like.

Examples of the monovalent group represented by A include phenylamino group, diphenylamino group, ethoxycarbonyl piperazino group, arylthio group and the like.

Y represents a nonmetallic atom necessary for forming a 5- to 10-membered heterocyclic ring, preferably, a 5- or 6-membered heterocyclic ring (the heterocyclic ring may be a condensed ring). Examples of the 5- to 10-membered heterocyclic ring formed by Y include the following rings: thiazole ring (such as thiazole, 4-methylthiazole and the like), benzothiazole ring (such as benzothiazole, 4-chlorobenzothiazole and the like), naphthothiazole ring (such as naphtho[2,1-d]thiazole, naphtho[1,2-d]thiazole and the like), thiazoline ring (such as thiazoline, 4-methylthiaazoline and the like), oxazole ring (such as oxazole, 4-nitrooxazole and the like), benzoxazole (such as benzoxazole, 4-chrolobenzoxazole and the like), naphthoxazole (such as naphtho[2,1-d]oxazole, naphtho[1,2-d]oxazole and the like), selenazole ring (such as selenazole, 4-phenyl selenazole and the like), benzoselenazole ring (such as benzoselenazole, 4-chrolobenzoselenazole), naphtoselenazole ring (such as naphtho[2,1-d]selenazole, naphtho[1,2-d]selenazole and the like), 3,3-dialkylindolenine ring (such as 3,3-dinitroindolenine, 3,3-diethylindolenine, 3,3-dimethyl-5-nitroindolenine and the like), imidazole ring (such as 1-alkylimidazole, 1-alkyl-4-phenylimidazole and the like), pyridine ring (such as 2-pyridine, 5-methyl-2-pyridine and the like), quinoline ring (such as 2-quinoline, 3-methyl-2-quinoline and the like), imidazo[4,5-b]quinoxaline ring (such as 1,3-diethylimidazo[4,5-b]quinoxaline and the like) and the like. Preferred examples of the 5- to 10-membered heterocyclic ring formed by Y include 3,3-dialkylindolenine ring.

M represents hydrogen atom, a metal, quaternary ammonium salt, or other pharmaceutically acceptable salts. The "pharmaceutically acceptable salts" may be any salt which can form nontoxic salts with the compound represented by the general formula [I]. Examples include, for example, alkaline metal salt such as a sodium salt, a potassium salt and the like; alkaline-earth metal salt such as a magnesium salt, a calcium salt and the like; organic ammonium salt such as a ammonium salt, a triethyl ammonium salt, tributyl ammonium salt, pyridinium salt and the like; salt of amino acid such as lysine salt, arginine salt and the like. Particularly preferred is a sodium salt with a reduced toxicity to a living body.

The compound of the present invention may have one or more asymmetric carbon atoms depending on the kind of substituents. Sulfur atoms may act as asymmetric center. Any optical isomers in an optically pure form based on one or more asymmetric carbon atoms, any mixture of the above optical isomers, racemates, diastereomers based on two or more asymmetric carbon atoms, any mixture of the above diastereomers and the like fall within the scope of the present invention.

Specific examples of the compound of the present invention are shown below. However, the scope of the present invention is not limited by the following compounds.

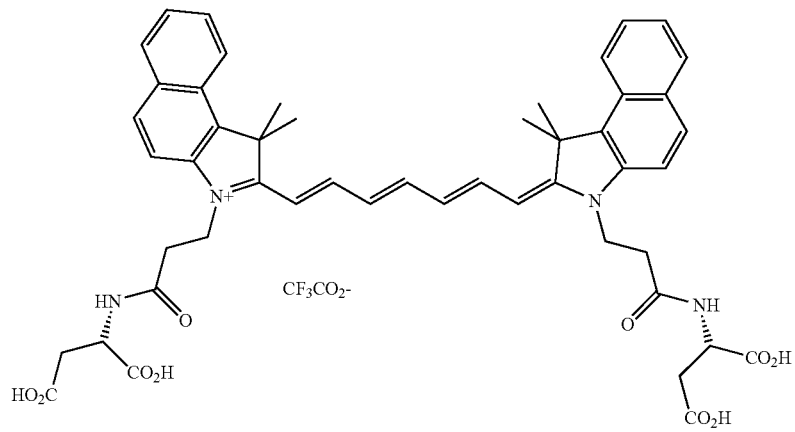

Compound 1

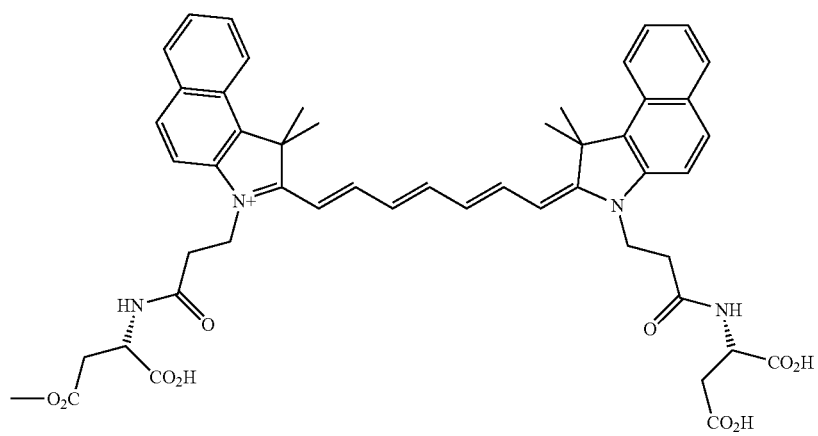

Compound 2

-continued
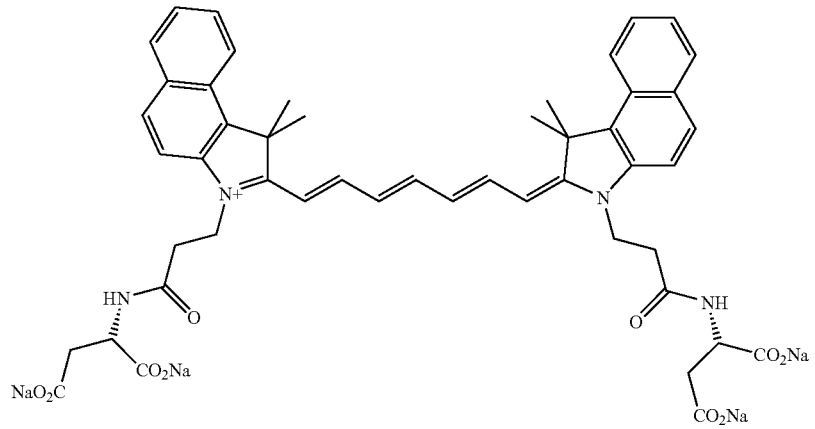
Compound 3
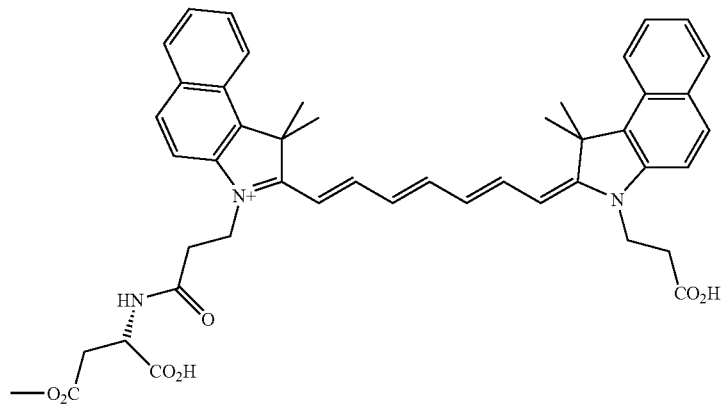
Compound 4
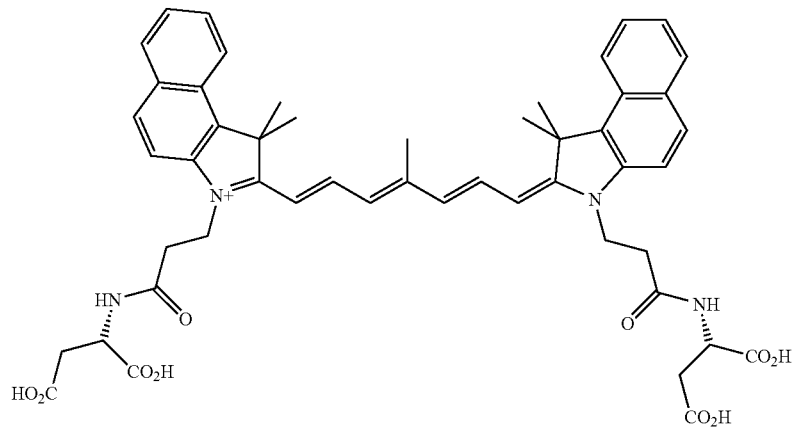
Compound 5

-continued
Compound 6
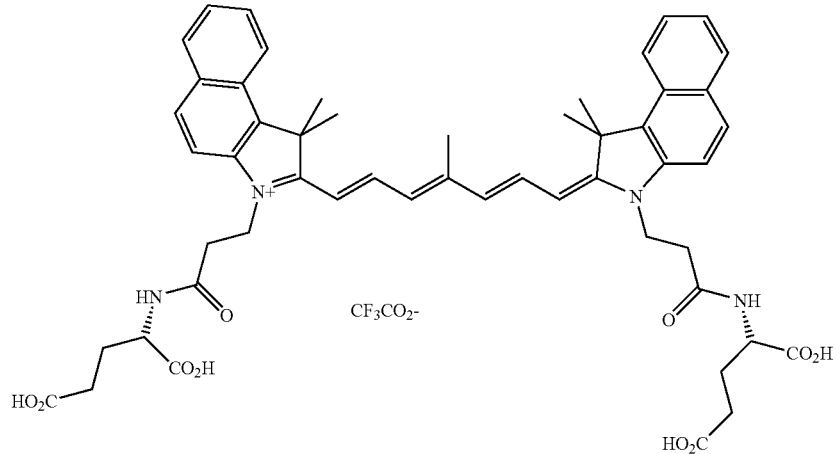
Compound 7
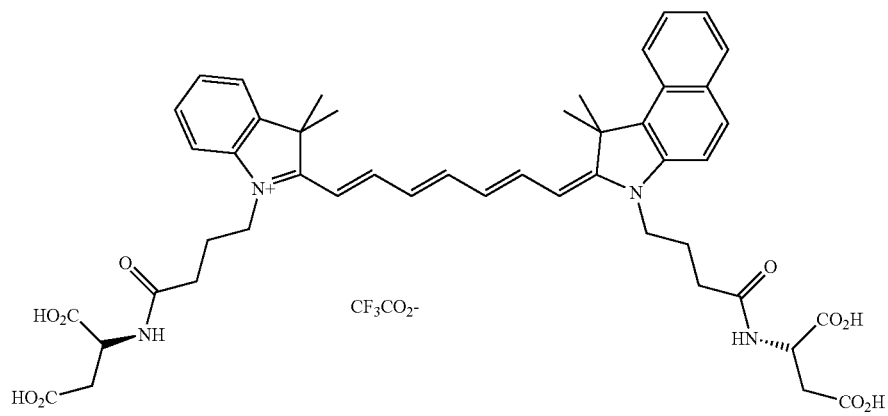
Compound 8
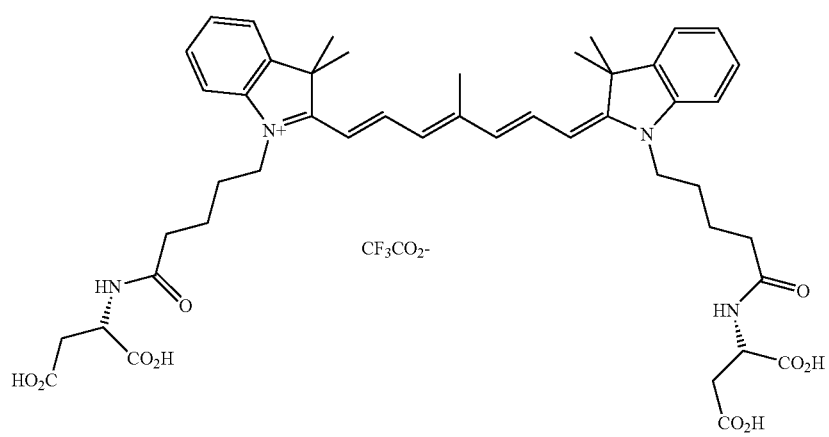

-continued
Compound 9
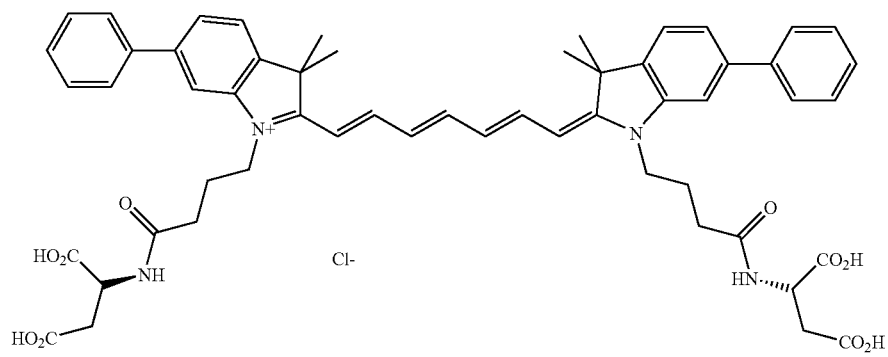
Compound 10
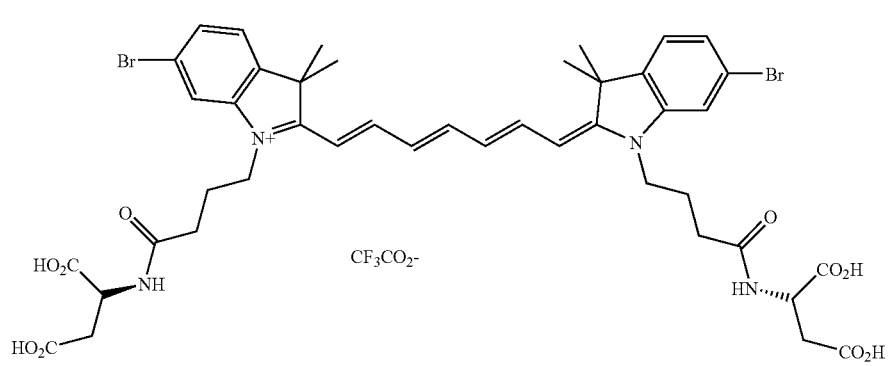
Compound 11
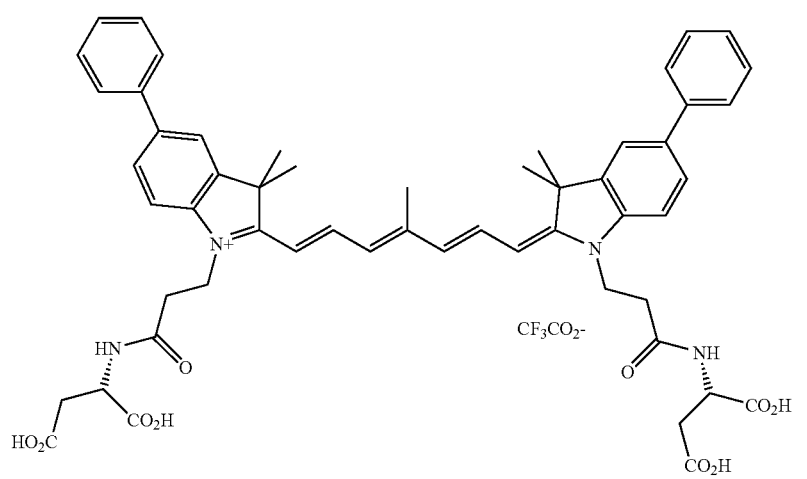
Compound 12
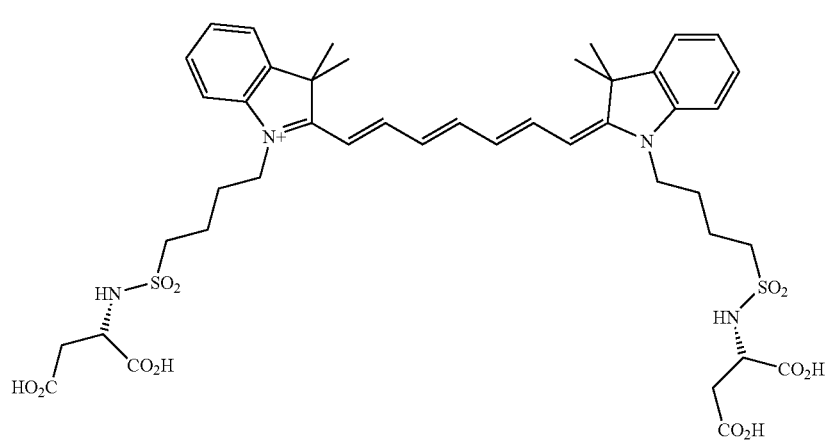

-continued
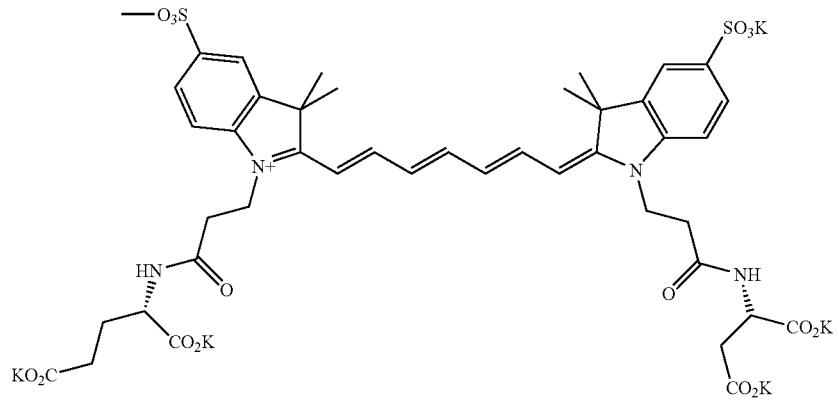
Compound 13
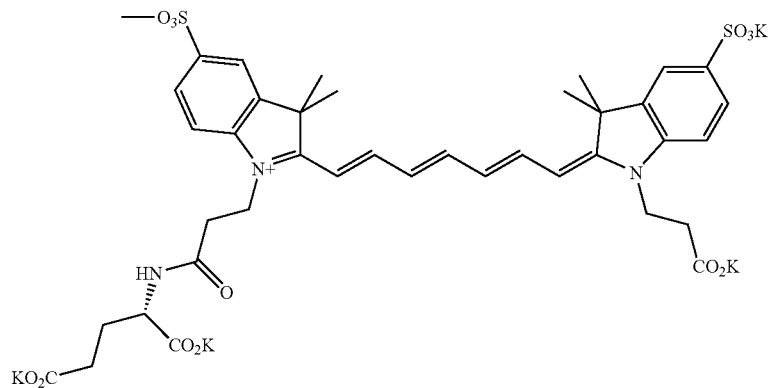
Compound 14
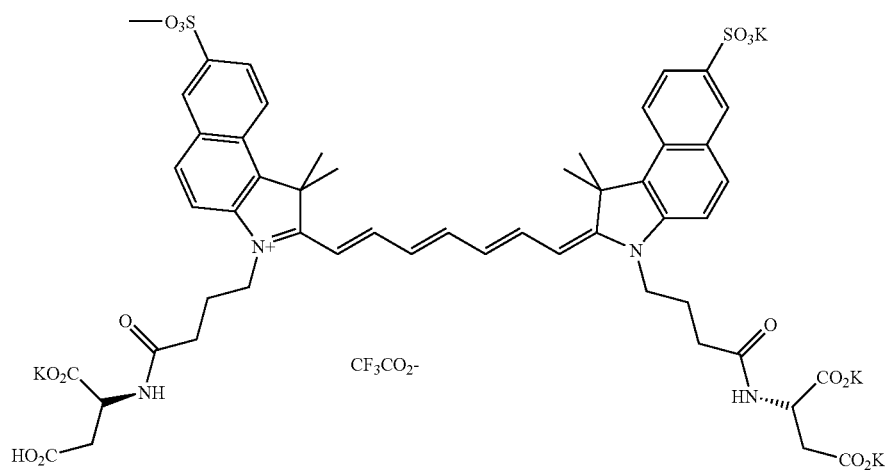
Compound 15

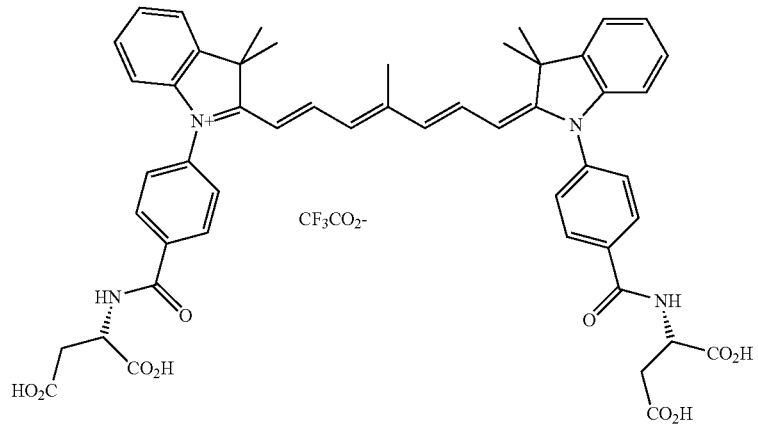
Compound 16
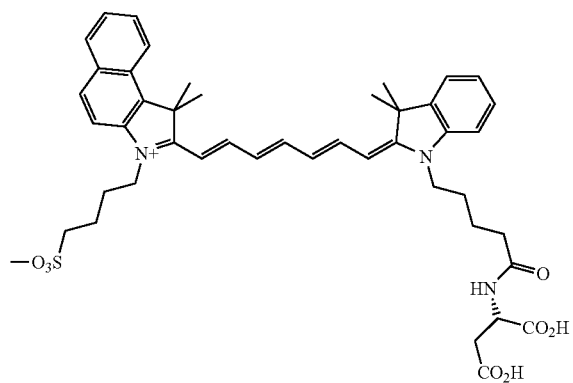
Compound 17
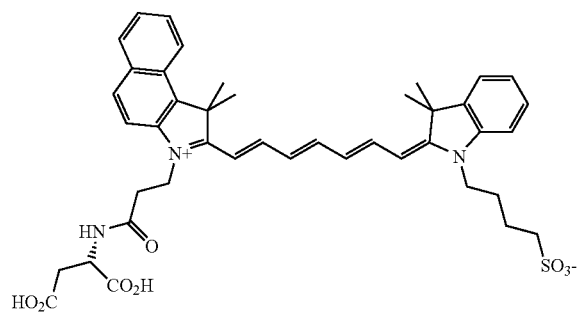
Compound 18
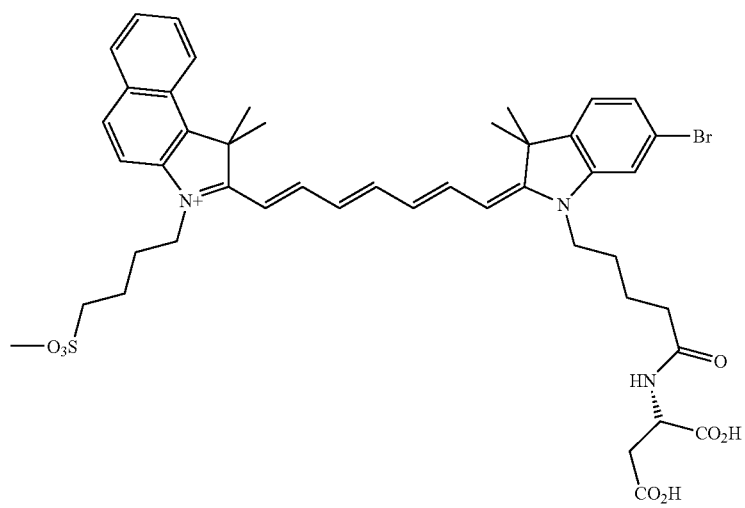
Compound 19

-continued
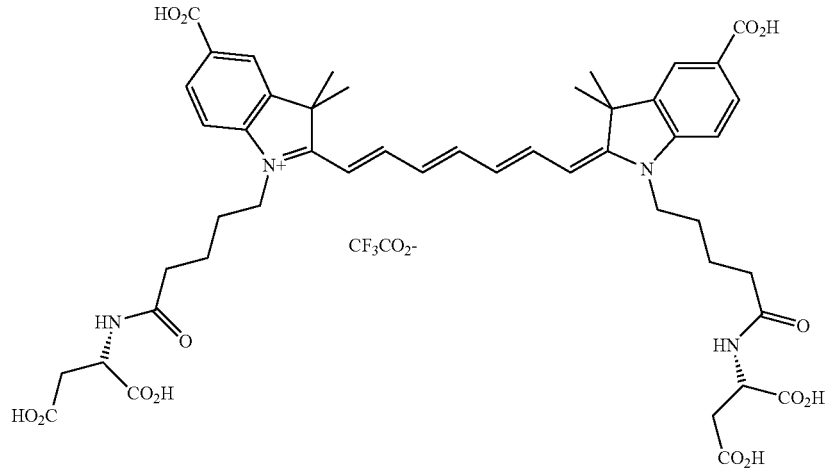
Compound 20
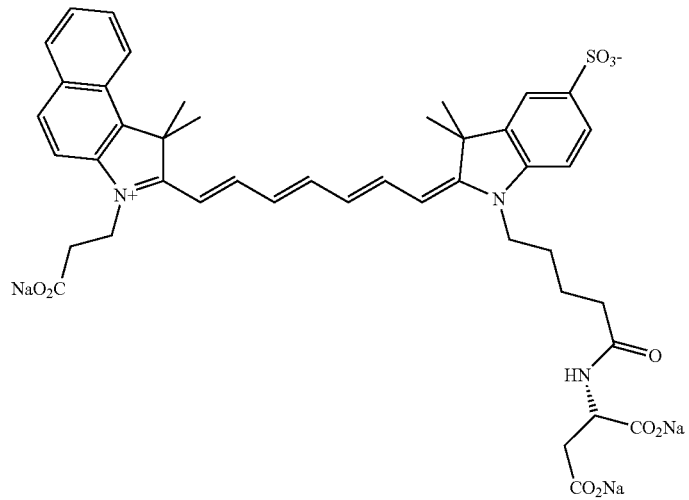
Compound 21
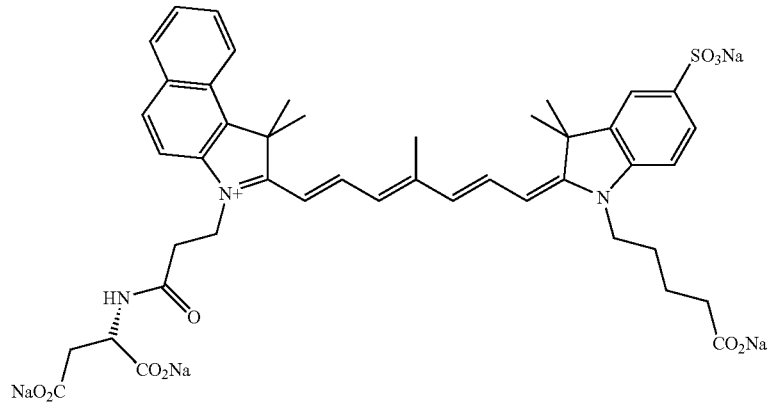
Compound 22

Compound 23
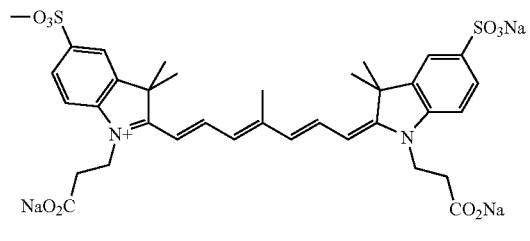
Compound 24
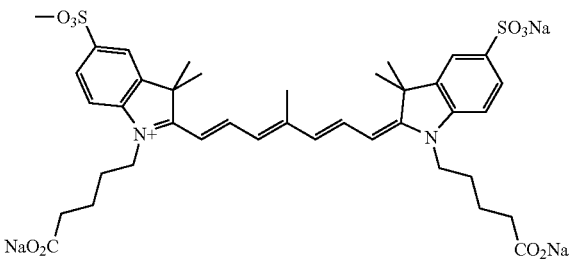
Compound 25
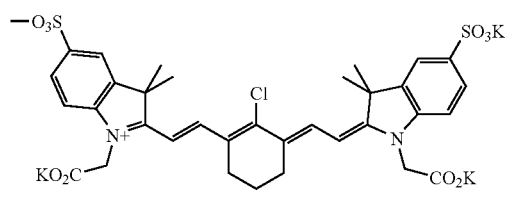
Compound 26
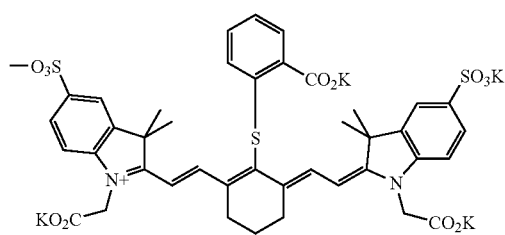
Compound 27
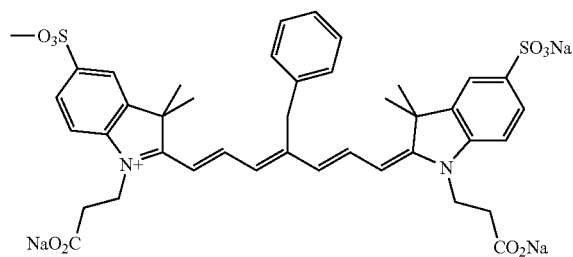
Compound 28
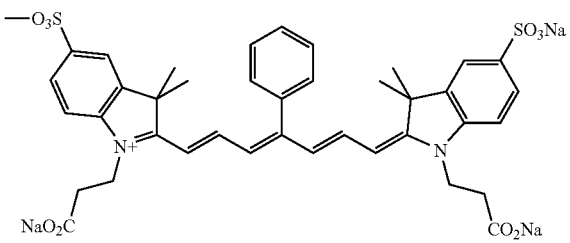
Compound 29
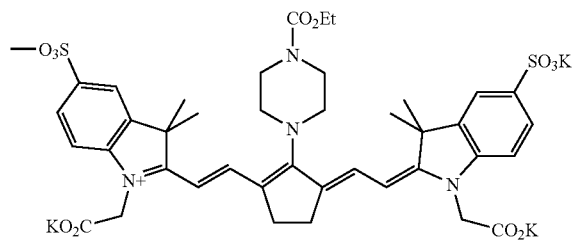
Compound 30
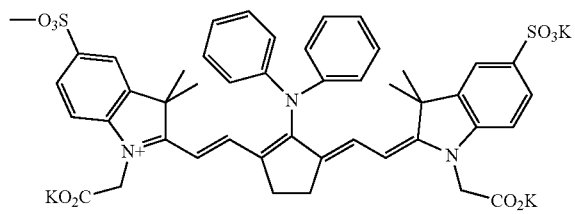
Compound 31
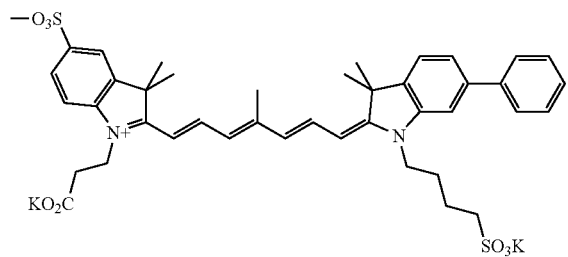
Compound 32
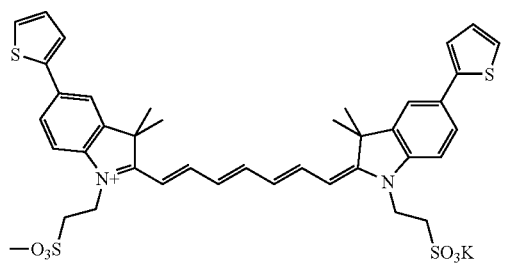

-continued

Compound 33

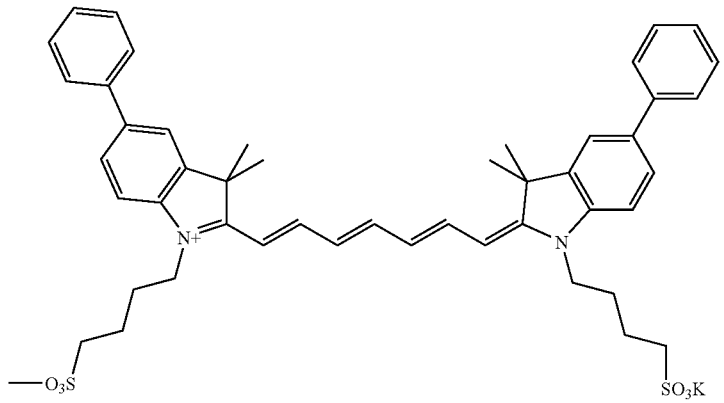

Compound 34

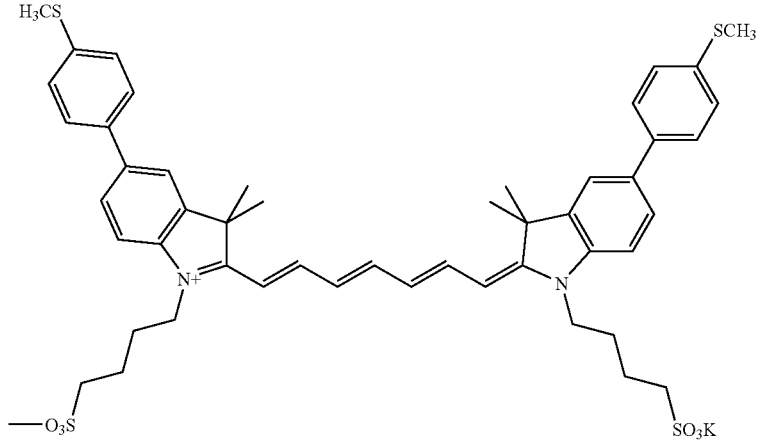

Compound 35

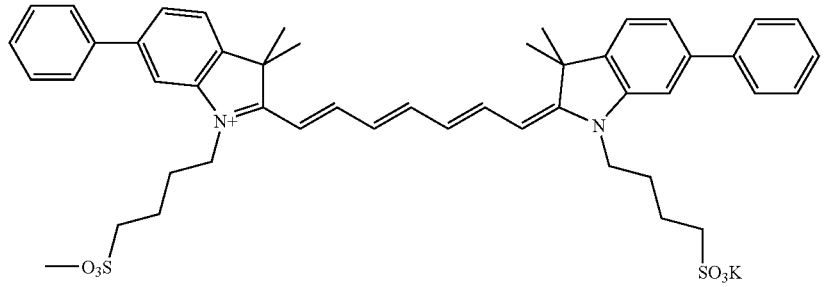

The cyanine dye-represented by the formula [I] or [II] can be synthesized according to known preparation methods of cyanine dye compounds, for example, those disclosed in the Cyanine Dyes and Related Compounds, F. M. Hamer, John Wiley and Sons, New York, 1964, Cytometry, 11, 416-430 (1990), Cytometry, 12, 723-730 (1990), Bioconjugate Chem, 4, 105-111 (1993), Anal. Biochem., 217, 197-204 (1994), Tetrahedron, 45, 4845-4866 (1989), EP-A-0591820A1, EP-A-0580145A1 and the like. Alternatively, they can be semisynthesized from a commercially available cyanine dye compound by known methods. More specifically, they can be synthesized by reacting a diaryl compound with a heterocyclic quaternary salt.

The methods for preparing the cyanine dye compounds represented by the above formula [I] or [II] are not particularly limited, and the compounds can be synthesized by various synthetic routes. Specific preparations of typical compounds of the present invention are disclosed in the Examples of the specification. Accordingly, one of ordinary skill in the art can prepare the cyanine dye compounds that falls within the scope of the above general formulas by referring to the methods described in the Examples, and if necessary, by adding appropriate alteration or modification to the methods and by appropriately choosing starting materials and reagents. For the preparation, a reaction selected from various reactions such as condensation, addition, oxidation, reduction and the like may be employed alone or in combination. These reactions are explained in detail in the literature. For example, various methods or material compounds described as unit synthetic operations in "Jikken Kagaku Kouza" (published by Maruzen, Ltd., each separate volume contained in the first to forth comprehensive edition is available) can be suitably used. In addition, syntheses of the compounds of the present invention are specifically described in the specification of PCT/JP01/06689, whose disclosures are herein incorporated by reference.

For example, where the above defined functional groups may change in a reaction step or they are not suitable to conduct a reaction step in the preparation, a desirable step can be sometimes conducted efficiently by utilizing various methods which are conventionally used in the field of organic synthetic chemistry, for example, means for protection or deprotection of functional groups, or treatments such as oxidation, reduction, hydrolysis and the like. Synthetic intermediate compounds and the target compounds in the above steps can be isolated and purified by conventional purification methods used in organic synthetic chemistry such as filtration, extraction, washing, drying, concentration, recrystallization, and various chromatography and the like. The synthetic intermediate products can be used in the next reaction without isolation.

As the active ingredient of the near infrared fluorescent contrast agent of the present invention, the compound represented by the general formula [I] or [II] or a salt thereof may be used alone or in combination. More specifically, the active ingredient may be contained in the contrast agent in a form of a suspension or a solution in a solvent such as injectable distilled water, physiological saline, Ringer's solution and the like. Additives such as pharmaceutically acceptable carrier, excipients and the like may also be formulated, if desired. Examples of these additives include substances such as pharmaceutically acceptable electrolytic solutions, buffering solutions, detergents, and substances for adjusting osmotic pressure, substances for improving stability or solubility such as cyclodextrin, liposome and the like. Any additives ordinarily available in the art may be used. The near infrared fluorescent contrast agent of the present invention is preferably synthesized through sterilization processes when used as a medicament for clinical application.

The contract agent can be administered to a living body by injection, spraying, or topical application such as intravascular application (venous, arterial), oral application, intraperitoneal application, percutaneous application, subcutaneous application, intracystical application, or intrabronchial application. Preferably, the contrast agent may be administered into blood vessels in the form of an aqueous solution, an emulsion or a suspension.

The dose of the near infrared fluorescent contrast agent of the present invention is not particularly limited insofar as the dose enables detection of a site to be diagnosed. The dose may appropriately be increased or decreased depending on the type of the compound to be used that emits near infrared fluorescence, the age, body weight and a target organ of a subjects to be administered and the like. Typically, the dose as the weight of the compound may be 0.1 to 100 mg/kg body weight, preferably 0.5 to 20 mg/kg body weight.

The contrast agent of the present invention may also be appropriately used for various animals other than human. A formulation for administration, the route of administration, a dose and the like may be appropriately chosen depending on the body weight and conditions of the target animals.

The compounds of the present invention represented by the above formula [I] and [II] have property to highly accumulated in tumor tissues. Utilizing said property, the present invention also provides the fluorescent contrast agent which enables specific imaging of a tumor tissue. In addition, the class of the compounds of the present invention have long-term retention in blood vessels, and therefore, the fluorescent contrast agent of the present invention is also useful for angiography.

The method for fluorescence imaging of the present invention is characterized by the use of the near infrared fluorescent contrast agent of the present invention. The method for imaging can be carried out by one of ordinary skill in the art according to known methods, and each of parameters such as excitation wavelength and fluorescence wavelength to be detected may appropriately be determined to achieve optimal imaging and evaluation, depending on the kind of near infrared fluorescence contrast agent to be administered and a subject to be administered. The period of time from administration of the near infrared fluorescent contrast agent of the present invention to the start of fluorescence imaging according to the present invention may vary depending on the kind of the near infrared fluorescent contrast agent to be used and a subject to be administered. For example, when the contrast agent comprising a compound of the formula [I] or formula [II] is administered for tumor imaging, a lapse time may be about 10 minutes to 24 hours after administration. When the lapse time is too short, fluorescence from every site may be still too intense and the target site is not distinguishable from other sites, and when the lapse time is too long, the contrast agent may be excreted from the body. When imaging of blood vessel is desired, the compound of the formula [I] or formula [II] is detected immediately after administration or in about 30 minutes after the administration.

For example, the fluorescence imaging can be conducted by the following steps. A near infrared fluorescent contrast agent of the present invention is administered to a subject to be diagnosed, and then the subject is exposed to an excitation light using an apparatus generating excitation light. Then, fluorescence from the near infrared fluorescent contrast agent, which is generated by the excitation light, is detected by using a fluorescence detector. The wavelength for excitation varies depending on the type of the near infrared fluorescent contrast agent to be used, and is not limited as long as the compounds efficiently emits fluorescence in the near infrared region. Preferably, a near infrared light having superior bio-permeability may be used. The wavelength of the near infrared fluorescence to be detected also varies depending on the contrast agent to be used. In general, an excitation light having a wavelength of 600 to 1000 nm, preferably 700 to 850 nm, may be used and near infrared fluorescence having a wavelength of 700 to 1000 nm, preferably, 750 to 900 nm, may be detected. As the apparatus for generating the excitation light, a conventional excitation light source such as various lasers (e.g., ion lased, dye laser and semiconductor laser), halogen light source, xenon light source and the like may be used. Various optical filters may be used to obtain optimal excitation wavelength, if desired. For detection of fluorescence, various optical filters may be used for selection of the fluorescence generated from the near infrared fluorescent contrast agent.

The detected fluorescence is data-processed as fluorescence information to construct fluorescence images to be recorded. Examples of the method for preparation of fluorescence images include, for example, a method comprising the step of irradiating the target tissue in a wide range, detecting fluorescence with a CCD camera, and then image-processing the fluorescence information obtained; a method using an optical CT device; a method using an endoscope; or a method using fundus oculi camera and the like.

According to the fluorescence imaging method of the present invention, systemic diseases, tumors, blood vessels and the like can be visualized without damaging a living body.

EXAMPLES

The present invention will be more specifically explained by referring to synthetic examples and a test example. However, the scope of the present invention is not limited to the following examples. In the examples, the serial numbers of the compounds correspond to that of the compounds listed in the above with chemical structures.

Example 1

Synthesis of Compound 1, Compound 2, and Compound 3

Synthetic route of Compound 1 is shown below.

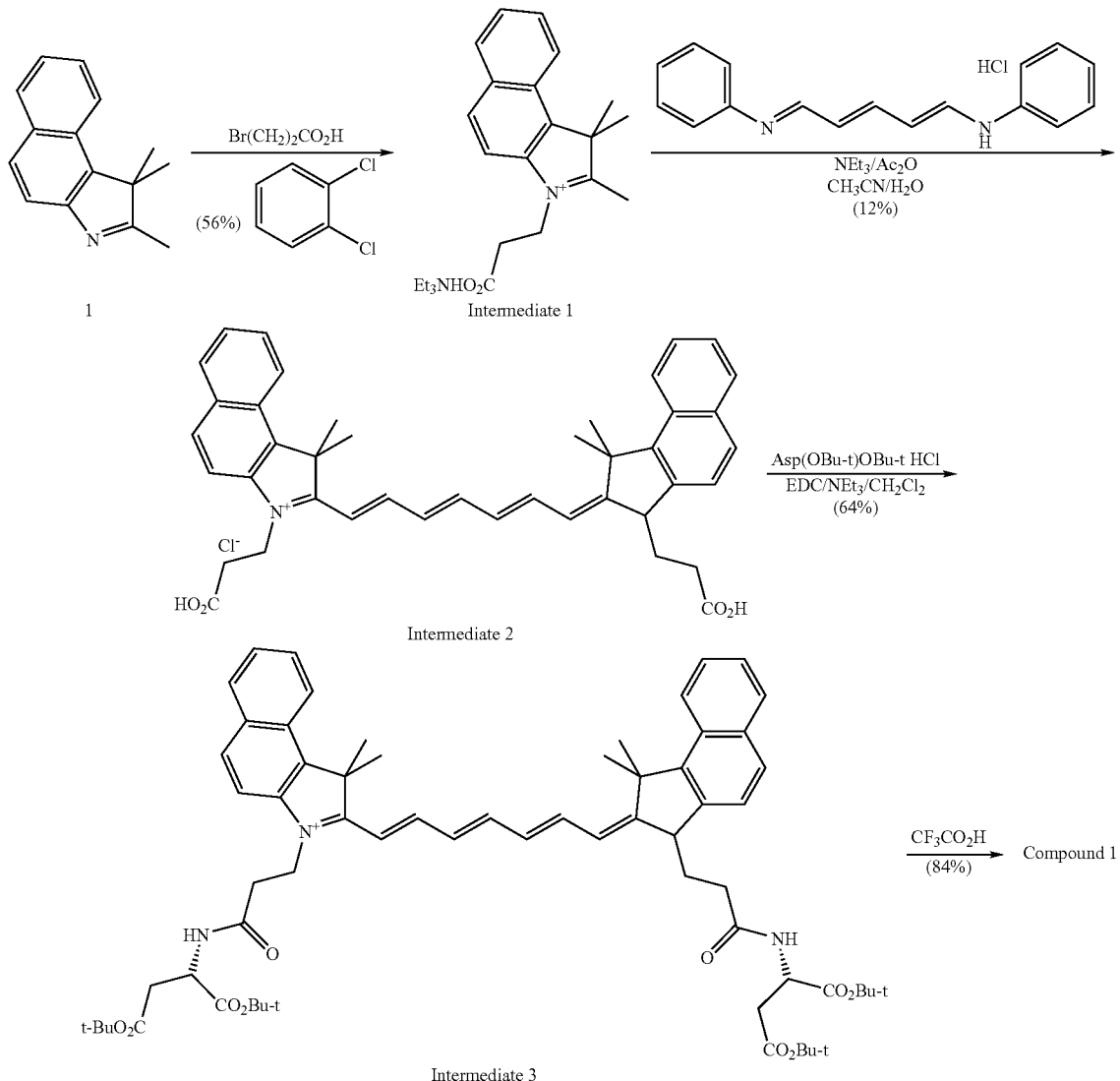

Synthesis of Intermediate 1

The starting material 1 (20.9 g, 0.1 mol), 2-bromopropinic acid (23.0 g, 0.15 mol), and o-dichlorobenzene (20 ml) were heated and stirred at 140° C. for 2 hours. After the reaction was completed, the reaction mixture was added with acetone (200 ml) and cooled to room temperature, and then the resultant crystal was filtrated to obtain Intermediate 1 (20.3 g, yield: 56%)

Synthesis of Intermediate 2

The Intermediate 1 obtained above (10.0 g, 28 mmol) and 1,7-diaza-1,7-diphenyl-1,3,5-heptatriene hydrochloride (3.9 g, 14 mmol) were dissolved in acetonitrile (70 ml) and water (11 ml), and the resulting solution was added with triethylamine (8.4 g, 91 mmol) and acetic anhydride (8.5 g, 91 mmol) and the mixture was stirred at room temperature for overnight. The reaction mixture was added to 0.1N hydrochloric acid (900 ml) dropwise and the crystals precipitated were filtrated. The crystal was purified by column chromatography (eluent:methylene chloride:methanol=95:5~90:10) to obtain Intermediate 2 (2.1 g, yield: 12%)

Synthesis of Intermediate 3

The Intermediate 2 obtained above (21.0 g, 1.5 mmol), L-aspartic acid-di-t-butylester monohydrate (1.3 g, 4.5 mmol), 4-dimethylaminopyridine (40 mg, 0.3 mmol) were dissolved in methylene chloride (50 ml) and the solution was cooled on ice. The resultant solution was added with 1-ethyl-3-(3-dimethylaminopropyl)carbodiimide hydrochloride (EDC) (700 mg, 4 mmol) and triethylamine (340 mg, 3 mmol), and stirred at 4° C. for overnight. The reaction mixture was added with methylene chloride (200 ml) and 1N hydrochloric acid (200 ml), and then the methylene chloride layer is extracted and washed with saturated sodium chloride solution (200 ml) and dried over sodium sulfate. The solvent was evaporated under reduced pressure and purified by column chromatography (eluent:ethyl acetate:methanol=95:5 to 80:20) to obtain Intermediate 3 (1.1 g, yield: 64%)

Synthesis of Compound 1, Compound 2, and Compound 3

Intermediate 3 (500 mg, 0.5 mmol) was dissolved in trifluoroacetic acid (5 ml) and reacted at 4° C. for overnight, and then trifluoroacetic acid was evaporated under reduced pressure. The resulting residue was added with water (50 ml) and then the resulting crystals were collected by filtration and washed with water and ethyl acetate to obtain Compound 1 (390 mg, yield: 90%).

Compound 1 was purified by column chromatography using Sephadex (LH-20, Pharmacia) (eluent:methanol) to obtain Compound 2.

Compound 1 was applied to an ion exchange resin column CR 11 (Mitsubishi Chemical, Co., Ltd.) to obtain Compound 3.

Compound 1
$^1$H-NMR (CD$_3$OD) δ 1.98 (s, 12H), 2.70 (d, J=7.2 Hz, 4H), 2.80 (t, J=7.2 Hz, 4H), 3.30 (MeOH), 4.50 (t, J=7.2 Hz, 4H), 4.60 (t, J=7.2 Hz, 2H), 4.80 (H$_2$O), 6.40 (d, J=13.2 Hz, 2H), 6.63 (dd, J=13.2, 13.2 Hz, 2H), 7.40-7.50 (m, 2H), 7.58-7.66 (m, 5H), 7.95-8.07 (m, 6H), 8.20 (d, J=7.2 Hz, 2H)

Compound 2
$^1$H-NMR (CD$_3$OD) δ 1.99 (s, 12H), 2.72 (d, J=7.2 Hz, 4H), 2.80 (t, J=7.2 Hz, 4H), 3.30 (MeOH), 4.50 (t, J=7.2 Hz, 4H), 4.60 (t, J=7.2 Hz, 2H), 4.80 (H$_2$O), 6.38 (d, J=13.2 Hz, 2H), 6.61 (dd, J=13.2, 13.2 Hz, 2H), 7.40-7.50 (m, 2H), 7.58-7.67 (m, 5H), 7.96-8.07 (m, 6H), 8.21 (d, J=7.2 Hz, 2H)

Compound 3
$^1$H-NMR (CD$_3$OD) δ 1.98 (s, 12H), 2.56-2.65 (m, 4H), 2.75-2.85 (m, 4H), 3.30 (MeOH), 4.45-4.50 (m, 4H), 4.80 (H$_2$O), 6.20 (d, J=13.2 Hz, 2H), 6.65 (dd, J=13.2, 13.2 Hz, 2H), 7.40-7.50 (m, 2H), 7.58-7.70 (m, 5H), 7.95-8.07 (m, 6H), 8.20 (d, J=7.2 Hz, 2H)

Example 2

Synthesis of Compound 5

Compound 5 was synthesized from Intermediate 1 and 1,7-diaza-5-methyl-1,7-diphenyl-1,3,5-heptatriene monohydrate in a similar manner to that for Compound 1.
$^1$H-NMR (CD$_3$OD) δ 2.00 (s, 12H), 2.44 (s, 3H), 2.73 (d, J=7.2 Hz, 4H), 2.82 (t, J=7.2 Hz, 4H), 3.31 (MeOH), 4.50 (t, J=7.2 Hz, 4H), 4.69 (t, J=7.2 Hz, 2H), 4.88 (H$_2$O), 6.41 (d, J=13.2 Hz, 2H), 6.65 (d, J=13.2 Hz, 2H), 7.43-7.50 (m, 2H), 7.58-7.67 (m, 4H), 7.95-8.05 (m, 4H), 8.10-8.27 (m, 4H)

Example 3

Synthesis of Compound 6

Compound 6 was synthesized from Intermediate 1 and 1,7-diaza-5-methyl-1,7-diphenyl-1,3,5-heptatriene monohydrate in a similar manner to that for Compound 1 except that L-glutamic acid-di-t-butylester monohydrate was used instead of L-aspartic acid-di-t-butylester monohydrate.
$^1$H-NMR (CD$_3$OD) δ 1.80-2.15 (m, 4H), 2.01 (s, 12H), 2.28 (t, J=7.2 Hz, 4H), 2.44 (s, 3H), 2.82 (t, J=7.2 Hz, 4H), 3.31 (MeOH), 4.40-4.50 (m, 2H), 4.51 (t, J=7.2 Hz, 4H), 4.88 (H$_2$O), 6.42 (d, J=13.2 Hz, 2H), 6.65 (d, J=13.2 Hz, 2H), 7.42-7.50 (m, 2H), 7.57-7.67 (m, 4H), 7.95-8.05 (m, 4H), 8.10-8.27 (m, 4H)

Example 4

Synthesis of Compound 7

Compound 7 was synthesized from 2,3,3-trimethylindolenine in a similar manner to that for Compound 1.
$^1$H-NMR (CD$_3$OD) δ 1.70 (s, 12H), 2.05-2.13 (m, 4H), 2.55 (t, J=7.2 Hz, 4H), 2.78-2.92 (m, 4H), 3.30 (MeOH), 4.10 (t, J=7.2 Hz, 4H), 4.89 (H$_2$O), 6.45 (d, J=13.2 Hz, 2H), 6.50 (J=13.2 Hz, 2H), 7.29-7.50 (m, 8H), 7.92 (dd, J=13.2, 13.2 Hz, 2H)

Example 5

Synthesis of Compound 8

Compound 8 was synthesized from 2,3,3-trimethylindolenine in a similar manner to that for Compound 1 except that 1,7-diaza-5-methyl-1,7-diphenyl-1,3,5-heptatriene monohydrochloride was used instead of 1,7-diaza-1,7-diphenyl-1,3,5-heptatriene monohydrate.
$^1$H-NMR (CD$_3$OD) δ 1.70 (s, 12H), 1.72-1.90 (m, 8H), 2.35-2.39 (m, 7H), 2.73-2.84 (m, 4H), 3.30 (MeOH), 4.08 (t, J=7.2 Hz, 4H), 4.66 (t, J=7.2 Hz, 2H), 4.89 (H$_2$O), 6.33 (d, J=13.2 Hz, 2H), 6.63 (d, J=13.2 Hz, 2H), 7.18-7.50 (m, 8H), 8.05 (dd, J=13.2, 13.2 Hz, 2H)

Example 6

Synthesis of Compound 9

Compound 9 was synthesized from 6-phenyl-2,3,3-trimethylindolenine (synthesized by a method described in the specification of the U.S. Pat. No. 6,004,536) in a similar manner to that for Compound 1.
$^1$H-NMR (CD$_3$OD) δ 1.75 (s, 12H), 2.05-2.15 (m, 4H), 2.45-2.55 (m, 4H), 2.75-2.84 (m, 4H), 3.30 (MeOH), 4.20 (t, J=7.2 Hz, 4H), 4.80 (H$_2$O), 6.38 (J=13.2 Hz, 2H), 6.62 (J=13.2 Hz, 2H), 7.43-7.70 (m, 17H), 7.95 (dd, J=13.2, 13.2 Hz, 2H)

Example 7

Synthesis of Compound 10

Compound 10 was synthesized from 6-bromo-2,3,3-trimethyl-indolenine in a similar manner to that for Compound 1.
$^1$H-NMR (CD$_3$OD) δ 1.68 (s, 12H), 2.00-2.15 (m, 4H), 2.40-2.55 (m, 4H), 2.77-2.92 (m, 4H), 3.30 (MeOH), 4.08 (t, J=7.2 Hz, 4H), 4.82 (m, 2H), 6.38 (J=13.2 Hz, 2H), 6.65 (J=13.2 Hz, 2H), 7.30-7.40 (m, 4H), 7.50-7.72 (m, 3H), 7.90-8.02 (m, 2H)

Example 8

Synthesis of Compound 11

Compound 11 was synthesized from 5-phenyl-2,3,3-trimethyl-indolenine in a similar method to that for Compound 1.

$^1$H-NMR (CD$_3$OD) δ 1.78 (s, 12H), 2.39 (s, 3H), 2.70-2.84 (m, 8H), 3.30 (MeOH), 4.30-4.46 (m, 4H), 4.60-4.68 (m, 2H), 6.39 (J=13.2 Hz, 2H), 6.66 (J=13.2 Hz, 2H), 7.30-7.48 (m, 9H), 7.56-7.72 (m, 3H), 8.05 (J=13.2 Hz, 13.2 Hz)

Example 9

Synthesis of Compound 13 and Compound 14

Synthetic route of Compound 13 and Compound 14 is shown below.

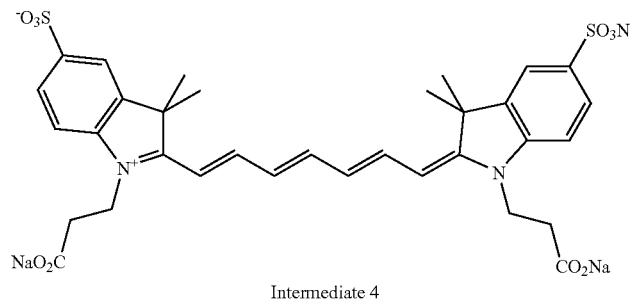

Intermediate 4

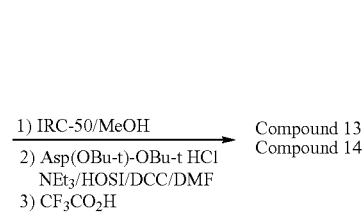

An intermediate compound (375 mg), which was obtained by reacting 5-sulfo-2,3,3-trimethylindolenine (prepared according to the method described in the Japanese Patent Unexamined Publication (KOKAI) No. (Hei)2-233658) and 1,7-diaza-1,7-diphenyl-1,3,5-heptatriene monohydrochloride in methanol in the presence of triethylamine and acetic anhydride, was dissolved in 5 ml of methanol, and then applied to an column filled with cationic ion exchange resin IRC-50 (Organo, eluent:methanol). The solvent was evaporated to give the proton form of the carboxylic acid. The resulting product was dissolved in 3 ml of dimethylformamide, and the solution was added with 338 mg (1.2 mmol) of dibutyl aspartate hydrochloride, 24 mg (0.2 mmol) of dimethylaminopyridine, and 121 mg (1.2 mmol) of triethylamine, and then the mixture was cooled on ice bath. The mixture was added with 230 mg (2 mmol) of hydroxysuccinimide (HOSI) and 288 mg (1.4 mmol) of N,N-dicyclohexylcarbodiimide (DCC), and the resulting mixture was stirred overnight. The reaction mixture was added with 200 ml of a mixed solvent of ethyl acetate/hexane (1:1) and crystals precipitated were collected by filtration. The crystals were purified by column chromatography (eluent:methylene chloride:methanol=10:1 to 2:1) to obtain diamide compound (135 mg) and monoamide compound (94 mg).

Each of the resulting diamide compound (120 mg) and monoamide compound (60 mg) was dissolved in 2 ml of trifluoroacetic acid, and then the mixture was stirred at room temperature for 1 hour. The reaction mixture was dissolved in water/methanol (1/1(v/v)) and purified by column chromatography using Sephadex (LH-20, Pharmacia, eluent:methanol). The resulting crystals were dissolved in a small volume of methanol, and the solution was added with a saturate solution of potassium acetate in methanol. Crystals precipitated were collected by filtration to obtain Compound 13 (35 mg, yield 7%) and Compound 14 (15 mg, yield 5%).

Compound 13

$^1$H-NMR (D$_2$O) δ 1.73 (s, 12H), 2.50-2.65 (m, 4H), 2.68-2.73 (m, 4H), 4.28-4.38 (m, 4H), 4.39-4.50 (m, 2H), 4.90 (D$_2$O), 6.47 (d, J=13.2 Hz, 2H), 6.74 (t, J=13.2 Hz, 2H), 7.40-7.50 (m, 2H), 7.60 (t, J=13.2 Hz, 1H), 7.80-8.05 (m, 6H)

Compound 14

$^1$H-NMR (D$_2$O) δ 1.65 (s, 6H), 1.70 (s, 6H), 2.40 (d, J=7.2 Hz, 2H), 2.58 (t, J=7.2 Hz, 2H), 2.70 (t, J=7.2 Hz, 2H), 4.18-4.30 (m, 4H), 4.90 (D$_2$O), 6.18 (d, J=13,2 Hz, 1H), 6.34 (d, J=13.2 Hz, 1H), 6.48-6.62 (m, 2H), 7.20 (d, J=7.2 Hz, 1H), 7.30 (d, J=7.2 Hz, 1H), 7.48 (t, J=13.2 Hz, 1H), 7.68-7.95 (m, 6H)

Example 10

Synthesis of Compound 15

Synthetic route of Compound 15 is shown below.

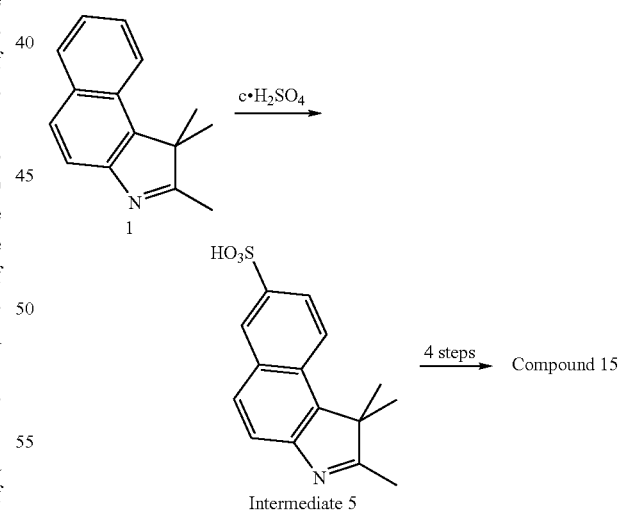

Intermediate 5

The starting material (41.8 g, 0.2 mol) was dissolved in conc. sulfuric acid (156 ml, 2.9 mol) and reacted at 140° C. for 1 hour, and then the mixture was cooled to 80° C. After the resulting solution was added to ice water (300 ml), a solution obtained by dissolving sodium hydroxide (96.6 g, 2.4 mol) in water (100 ml) was carefully added to the mixture. The crystals precipitated were collected by filtration and washed with water (120 ml). The resulting crude crystal was added with water (300 ml) and methanol (100 ml), and the mixture was refluxed under stirring for 30 minutes, and then cooled to room temperature. The resulting crystals were collected by filtration and washed with water (100 ml) and methanol (120 ml) to obtain Intermediate 5 (37.9 g, yield: 66%).

Compound 15 was obtained form Intermediate 5 in a similar method to that for Compound 13.

$^1$H-NMR (CD$_3$OD) δ 2.00 (s, 12H), 2.72 (d, J=7.2 Hz, 4H), 2.82 (t, J=7.2 Hz, 4H), 3.30 (MeOH), 4.58 (t, J=7.2 Hz, 4H), 4.70 (t, J=7.2 Hz, 4H), 4.86 (H$_2$O), 6.42 (d, J=13.2 Hz, 2H), 6.62 (dd, J=13.2, 13.2 Hz, 2H), 7.62-7.70 (m, 3H), 7.95-8.12 (m, 6H), 8.28 (d, J=7.2 Hz, 2H), 8.42 (s, 2H)

Example 11

Synthesis of Compound 23

Synthetic route of Compound 23 is shown below.

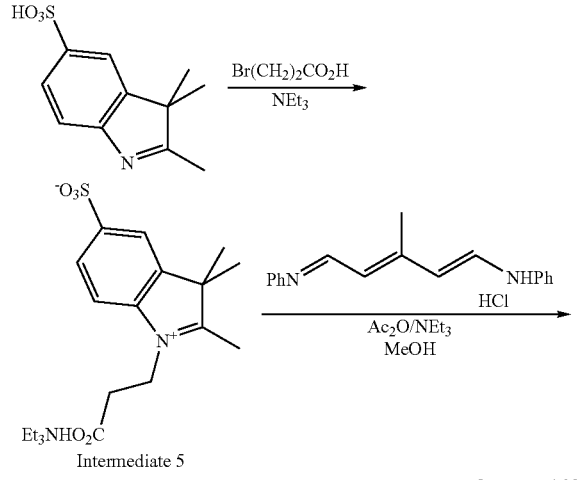

Synthesis of Intermediate 6

5-Sulfo-2,3,3-trimethylindolenine (synthesized according to the method described in Japanese Patent Unexamined Publication (KOKAI) No. (Hei) 2-233658) (24.0 g, 0.1 mol), 2-bromopropionic acid (23.0 g, 0.15 mol) and triethylamine (10.1 g, 0.1 mol) were heated and stirred at 160° C. for 6 hours. After the reaction was completed, the reaction mixture was added with methanol (200 ml) and cooled to room temperature, and then the resulting crystals were collected by filtration to obtain Intermediate 6 (6.0 g, yield: 19.3%).

Synthesis of Compound 23

The Intermediate 1 (3.1 g, 10 mmol) obtained above and 1,7-diaza-1,7-diphenyl-4-methyl-1,3,5-heptatriene monohydrochloride (Japanese Patent Unexamined Publication (KOKAI) No. (Hei) 8-295658) (1.5 g, 5 mmol) were dissolved in methanol (20 ml), and the resulting solution was added with triethylamine (2.5 g, 25 mmol) and acetic anhydride (4.6 g, 45 mmol) and the mixture was stirred at room temperature for 3 hours. The reaction mixture was added with sodium acetate (3.3 g, 33 mmol) and stirred at room temperature for 30 minutes. The resulting crystals were collected by filtration and washed with methanol (20 ml) to obtain Compound 23 (2.0 g, yield: 50.0%).

$^1$H-NMR (D$_2$O) δ (ppm) 1.60 (s, 12H), 2.30 (s, 3H), 2.60 (t, 4H, J=7.2 Hz), 4.20 (t, 4H, J=7.2 Hz), 6.25 (d, 2H, J=14.5 Hz), 6.55 (dd, 2H, 14.5, 14.5 Hz), 7.25 (d, 2H, J=7.0 Hz), 7.70-7.80 (m, 4H), 8.00 (dd, 2H, J=14.5, 14.5 Hz)

Example 12

Synthesis of Compound 25 and Compound 26

The synthetic route of Compound 25 and Compound 26 is shown below.

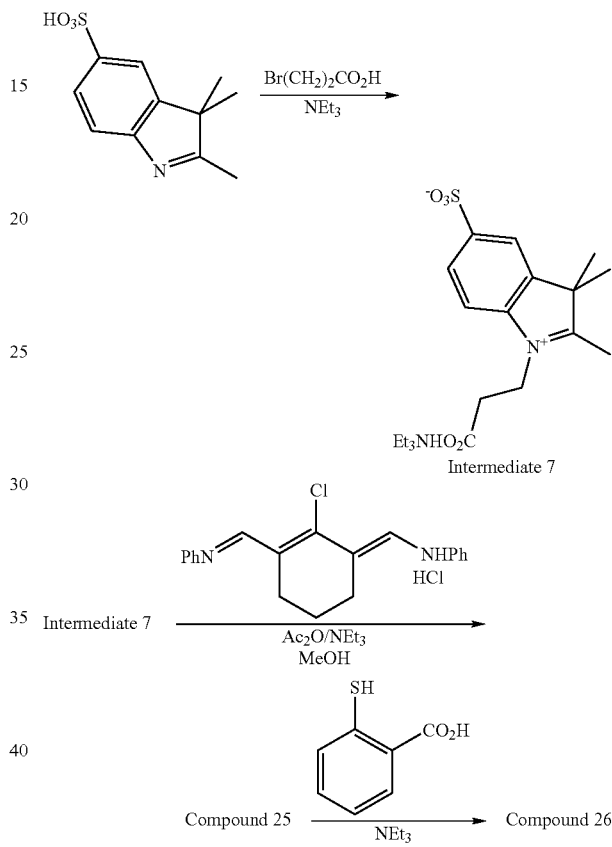

Synthesis of Intermediate 7

Intermediate 7 was synthesized from 5-sulfo-2,3,3-trimethylindolenine and bromoacetic acid in a similar method to that for Intermediate 6 (16.6 g).

Synthesis of Compound 25

Compound 25 was synthesized from Intermediate 7 and Intermediate 8 (obtained according to the method described in Zh. Org. Khim., 13, pp. 1189-1192, 1977) in a similar method to that for Compound 23 (15.0 g).

MS (FAB-, Glycerin) m/z=844

Synthesis of Compound 26 Compound 25 (4.2 g, 5 mmol) and triethylamine (1.0 g) was added to water (20 ml) and then the obtained solution was added with o-mercaptobenzoic acid (0.93 g, 6 mmol) and stirred at room temperature for 1 hour. The obtained mixture was added with potassium acetate (2.0 g, 20 mmol), and then added with ethanol (20 ml), the resultant crystal was filtered to obtain Compound 26 (1.3 g, yield: 27%)

MS (FAB-, Glycerin) m/z=962

Example 13

Synthesis of Compound 32

Synthetic route of Compound 32 is shown below.

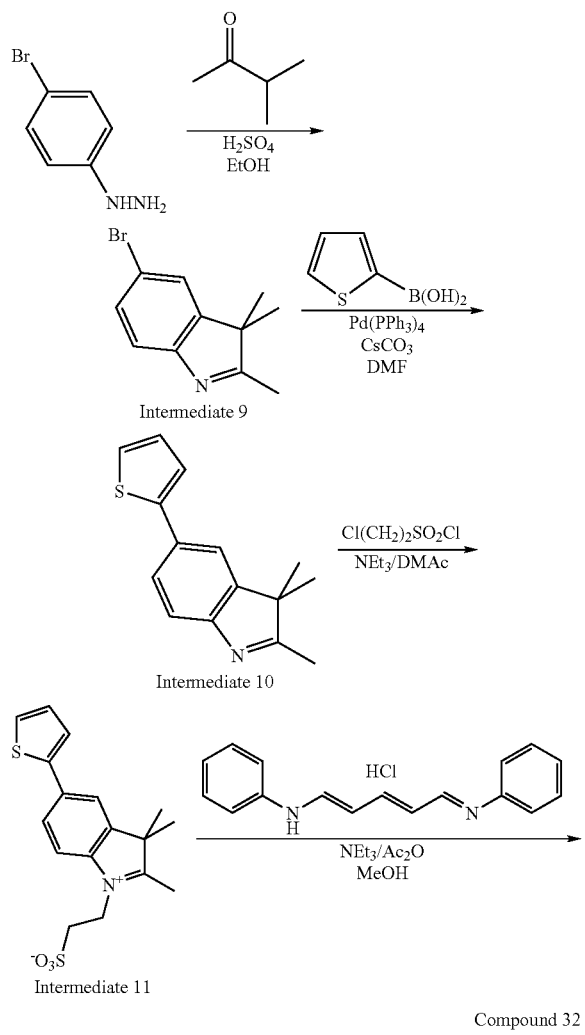

Synthesis of Intermediate 9

4-Bromophenylhydrozine monohydrochloride (73.8 g, 0.33 mmol) and 3-methyl-2-butanone (33.2 g, 0.40 mmol) were dissolved to ethanol (450 ml) and the resulting solution was added with conc. sulfuric acid (7.5 ml) and refluxed under stirring for 8 hours. After the mixture was cooled to room temperature, the solution was concentrated to 100 ml under reduced pressure. To the residue, water (400 ml) and ethyl acetate (400 ml) were added, and then pH of the aqueous layer was adjusted to 7 to 8 with sodium hydroxide solution. The resulting solution was extracted with ethyl acetate, washed with saturated sodium chloride solution, and dried over anhydrous sodium sulfate. The resulting residue was purified by silica gel column chromatography (eluent:hexane:ethyl acetate=5:1 to 1:1) to obtain Intermediate 9 as a brown liquid (58.6 g, yield: 76%)

Synthesis of Intermediate 10

Intermediate 9 (4.76 g, 20 mmol) and thiophene boronic acid (3.84 g, 30 mmol) are added to dimethyl formamide (50 ml) and the resulting solution was added with palladium tetraxis phenylphosphine (1.16 g, 9 mmol) and cesium chloride (13.3 g, 40 mmol) and heated and stirred under nitrogen atmosphere at 100° C. for 4 hours. After water (200 ml) was added, the mixture was extracted with ethyl acetate (200 ml) and washed with saturated sodium chloride solution, and then the organic layer was dried over anhydrous sodium sulfate and evaporated under reduced pressure. The residue was purified by silica gel column chromatography (eluent:hexane:ethyl acetate=2:1 to 1:1) to obtain Intermediate 10 as a brown solid (2.8 g, yield: 58%).

Synthesis of Intermediate 11

Intermediate 10 (1.40 g, 6 mmol) and triethylamine (0.59 g, 6 mmol) are added to dimethyl formamide (3 ml), and the mixture was added dropwise with 2-chloroethane sulfonyl-chloride (1.42 g, 9 mmol) under ice cooling After stirring was continued at room temperature for 30 minutes, the solution was added with a solution obtained by dissolving sodium hydroxide (0.23 g, 6 mmol) to water (2 ml) and further stirred at room temperature for 1 hour. To the mixture, ethyl acetate was added, and the upper layer was removed by decantation. The residue was dried to obtain Intermediate 11. The Intermediate 11 was used in the next reaction without further purification.

Synthesis of Compound 32

The Intermediate 11 obtained above and 1,7-diaza-1,7-diphenyl-1,3,5-heptatriene monohydrochloride were dissolved in methanol (5 ml) and the resulting solution was added with triethylamine (160 mg, 2 mmol) and anhydrous acetic acid (230 mg, 2 mmol), and then the mixture was stirred at room temperature for 7 hours. This mixture was added with ethyl acetate (20 ml) and the crystals precipitated were collected by filtration and washed with ethyl acetate (10 ml). This crystals were dissolved in methanol (10 ml) and then the solution was added with a saturated solution of potassium acetate in methanol (10 ml). The crystals precipitated were collected by filtration and washed with methanol (5 ml). The crystals were purified by Sephadex LH-20 (diluent:methanol) to obtain Compound 32 (15 mg, yield: 2% (from Intermediate 2).

$^1$H-NMR (CD$_3$OD) δ (ppm) 1.75 (s, 12H), 3.25 (t, 4H, J=7.2 Hz), 4.50 (t, 4H, J=7.2 Hz), 6.40 (d, 2H, J=14.5 Hz), 6.63 (dd, 2H, 14.5, 14.5 Hz), 7.07-7.12 (m, 2H), 7.33-7.45 (m, 6H), 7.53-7.75 (m, 5H), 7.96 (dd, 2H, J=14.5, 14.5 Hz) MS (FAB-, Glycerin) m/z=760

Example 14

Synthesis Compound 33

The synthetic route of compound 33 is shown below.

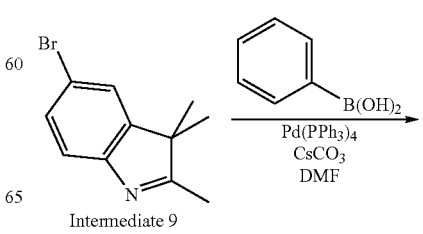

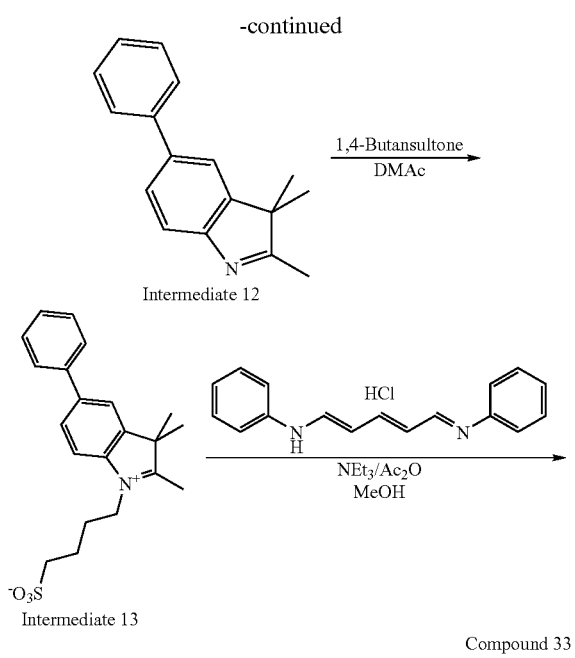

Synthesis of Compound 33

Intermediate 13 (1110 mg, 3 mmol) and 1,7-diaza-1,7-diphenyl-1,3,5-heptatriene monohydrochloride (285 mg, 1 mmol) were dissolved in methanol (5 ml), and the resulting solution was added with triethylamine (480 mg, 5 mmol) and anhydrous acetic acid (670 mg, 7 mmol) and then stirred at room temperature for 7 hours. Ethyl acetate (10 ml) was added to the reaction mixture and crystals precipitated were collected by filtration and washed with ethyl acetate (10 ml). The crystals were dissolved in methanol (5 ml) and added with a saturated solution of potassium acetate in methanol (10 ml), and the crystals precipitated were filtered and washed with 5 ml. The crystal was purified by Sephadex LH-20 (diluent; methanol) to obtain Compound 33 (250 mg, yield: 30%).

$^1$H-NMR (CD$_3$OD) δ (ppm) 1.80 (s, 12H), 1.95-2.05 (m, 8H), 2.90 (t, 4H, J=7.2 Hz), 4.20 (t, 4H, J=7.2 Hz), 6.38 (d, 2H, J=14.5 Hz), 6.62 (dd, 2H, 14.5, 14.5 Hz), 7.30-7.48 (m, 8H), 7.60-7.74 (m, 9H), 7.93(dd, 2H, J=14.5, 14.5 Hz) MS (FAB-, Nitrobenzylalcohol) m/z=803

Example 15

Synthesis of Compound 34

Compound 34 was synthesized from Intermediate 9 and 4-methyl mercaptophenyl boronic acid in a similar method to that for Compound 33 (15 mg).

$^1$H-NMR (CD$_3$OD) δ (ppm) 1.68 (s, 12H), 1.95-2.10 (m, 8H), 2.50 (s, 6H), 3.00 (t, 4H, J=7.2 Hz), 4.10 (t, 4H, J=7.2 Hz), 6.30 (d, 2H, J=14.5 Hz), 6.62 (dd, 2H, 14.5, 14.5 Hz), 7.20-7.70 (m, 19H)

Example 16

Synthesis of Compound 35

Synthetic route of Compound 35 is shown below.

Synthesis of Intermediate 12

Intermediate 12 was synthesized from Intermediate 9 and dihydroxyphenyl borane in a similar method of that for Intermediate 10 (3.6 g, yield: 77%).

Synthesis of Intermediate 13

Intermediate 12 (1.40 g, 6 mmol) and 1,4-butanesaltone (1.22 g, 9 mmol) were dissolved in dimethyl acetamide (2 ml) and the solution was stirred at 135° C. for 5 hours. The solution was added with ethyl acetate (20 ml) and cooled to room temperature, and then the crystals precipitated were filtered and washed with ethyl acetate to obtain Intermediate 13 (10 ml) (1.84 g, yield: 84%).

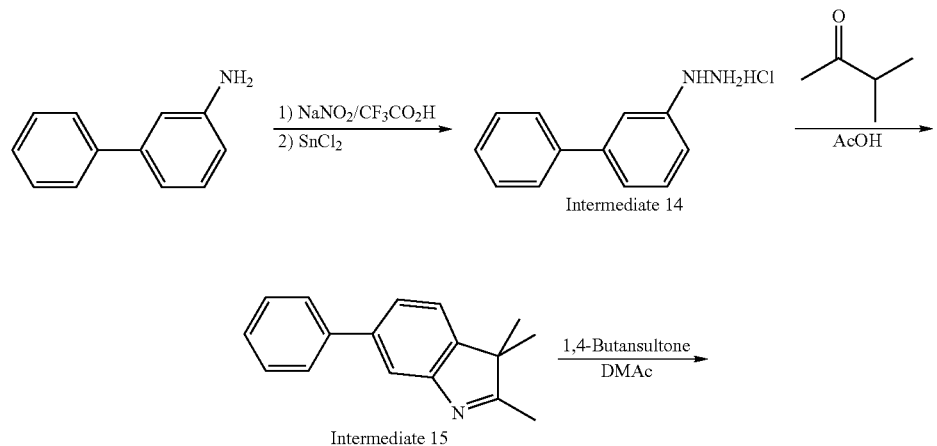

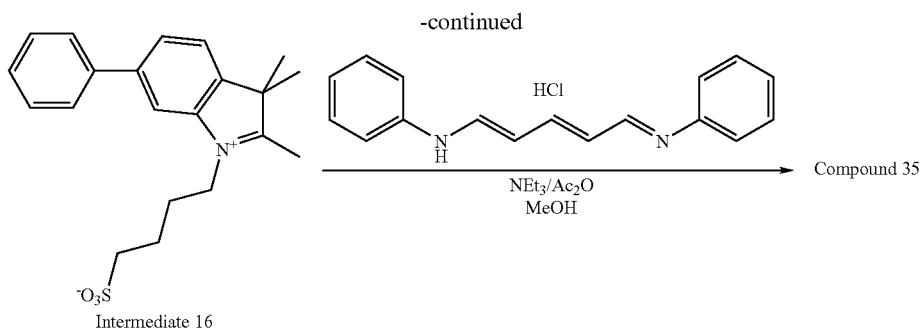

Intermediate 16

Synthesis of Intermediate 14

25.0 g of 3-aminodiphenyl (0.15 mol) was added to 100 ml of trifluoroacetic acid, and the mixture was cooled to the internal temperature of 0° C. The mixture was added dropwise with a solution obtained by dissolving 10.2 g of sodium nitrite (0.15 mol) in 100 ml of water while the temperature of the reaction mixture was kept below 5° C. After the dropwise addition was completed, the mixture was stirred at the same temperature for 15 minutes, and then the mixture was added with a solution obtained by dissolving 100 g of stannic chloride (0.54 mol) in 50 ml of concentrated hydrochloric acid while the temperature of the reaction mixture was kept below 10° C. After the completion of the dropwise addition, the crystals precipitated by addition of 250 ml of water were collected by filtration and washed with 200 ml of methylene chloride. The resulting Intermediate 14 was dried and used for the synthesis of Intermediate 15 without purification.

Synthesis of Intermediate 15

The above-obtained Intermediate 14 (whole amount) and 12.9 g of 3-methyl-2-butanone (0.15 mol) were added to 140 ml of acetic acid, and the mixture was heated under stirring for 2 hours and 30 minutes. After the mixture was cooled to room temperature, the crystals precipitated were removed by filtration, and the filtrate was concentrated under reduced pressure to one quarter volume. The residue was added with 300 ml of water and 300 ml of ethyl acetate, and insoluble precipitates were removed by filtration using celite. The filtrate was extracted with ethyl acetate (300 ml, 200 ml×2), and the extract was washed with a saturated sodium hydrogen carbonate solution and saturated brine, and then dried over sodium sulfate and the solvent was evaporated under reduced pressure. The resulting residue was purified by silica gel chromatography (eluent:hexane:ethyl acetate=3:1 to 2:1). The crystal obtained was recrystallized from 50 ml of hexane to obtain Intermediate 15. 1.3 g (yield: 4%)

Synthesis of Compound 35

Compound 35 was synthesized from Intermediate 15 in a similar method to that for Intermediate 13 and Compound 33 (65 mg).

MS (FAB-, Glycerin) m/z=842,804. $^1$H-NMR (D$_2$O) δ (ppm) 1.70 (s, 12H), 1.90-2.00 (m, 8H), 2.90 (t, 4H, J=7.2 Hz), 4.10 (t, 4H, J=7.2 Hz), 6.22 (d, 2H, J=14.5 Hz), 6.55 (dd, 2H, 14.5, 14.5 Hz), 7.30-7.60 (m, 17H), 7.77 (dd, 2H, J=14.5, 14.5 Hz)

Test Example 1

Fluorescence Imaging Test

Figure 2:
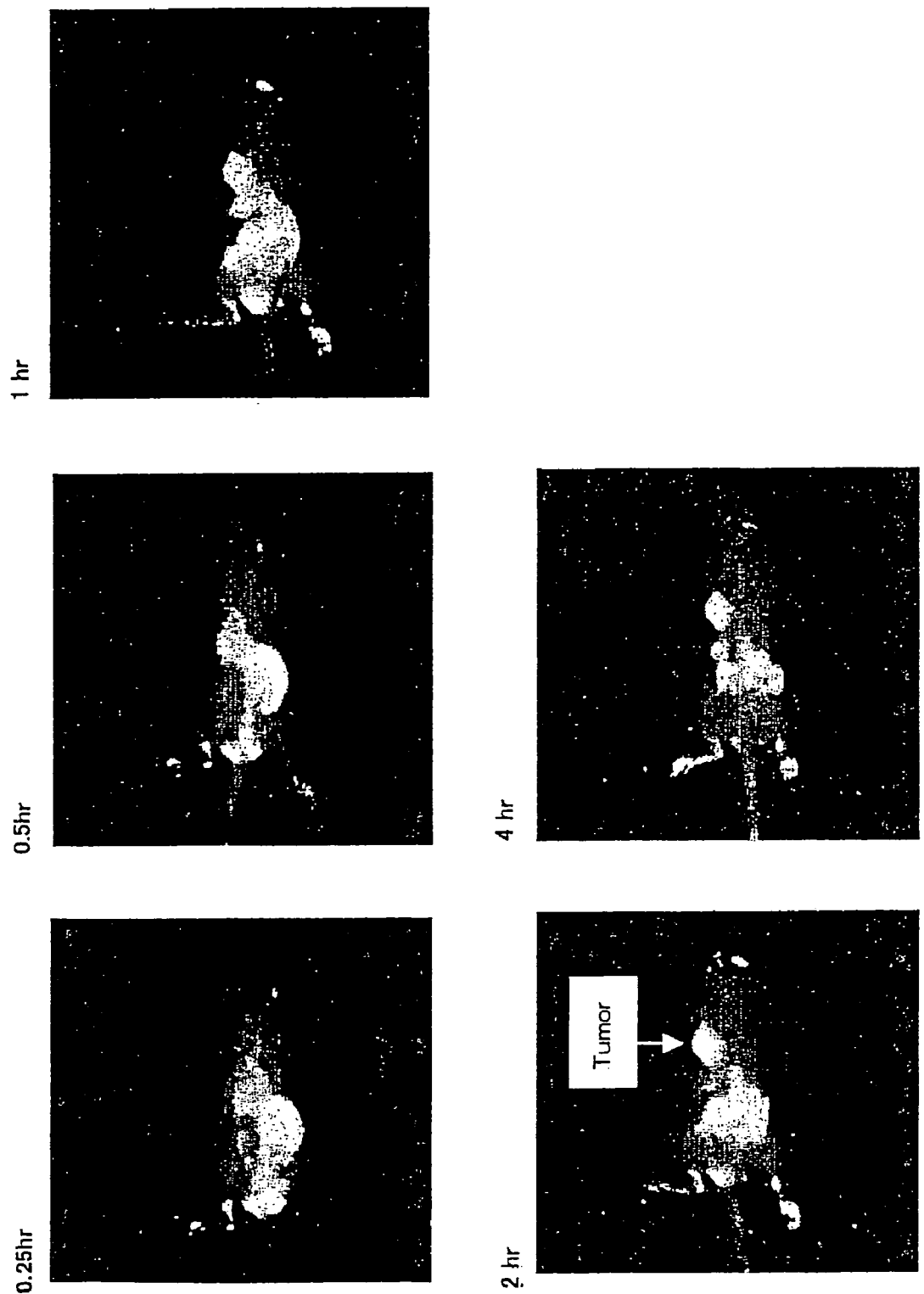
FIG. 2 is a photograph showing the results of fluorescence imaging at given times after the administration of ICG as a reference.
Figure 3:
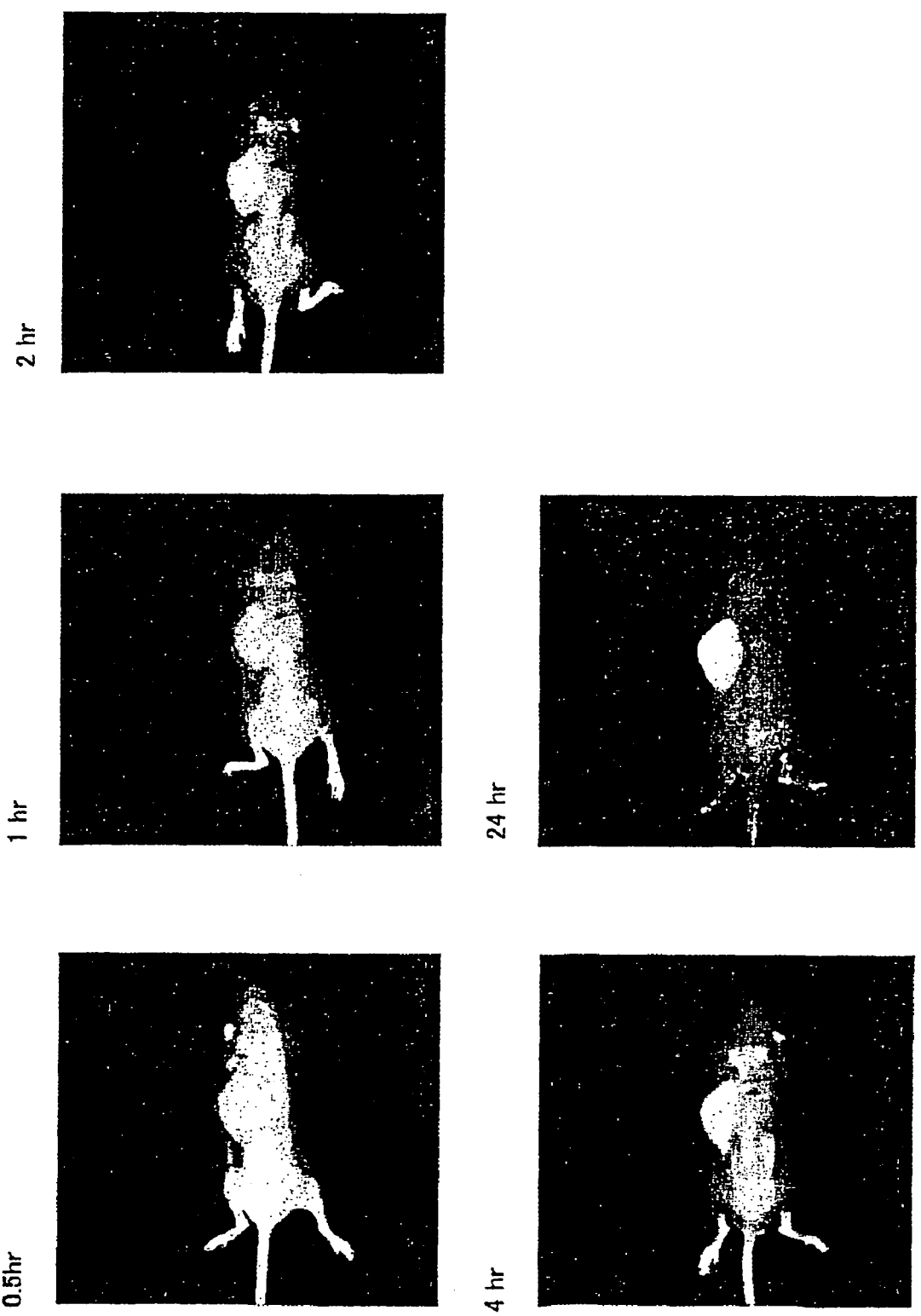
FIG. 3 is a photograph showing the results of fluorescence imaging at given times after the administration of Compound A as a reference.

Tumor tissue pieces of mouse colon carcinoma (colon 26 carcinoma) were subcutaneously grafted to the left breast of BALB/c nude mice (5 weeks old, Clea Japan, Inc.). Ten days later when the tumor grew to a diameter of about 8 mm, the mice were subjected to the test. As a fluorescence excitation light source, a titanium sapphire laser was used. The test mice were uniformly exposed to the laser light using a ring type light guide (Sumita Optical Glass Co.) wherein dispersion of irradiation was within 10%. The irradiation power output was adjusted so that the power was about 40 μW/cm$^2$ near skin surface of the mice. The fluorescence was excited at the maximum excitation wavelength of each compound and fluorescence emission from the mice was detected and photographed through a short wavelength cutoff filter (IR84, IR86, IR88, Fuji Photo Film CO., LTD.) with CCD camera (C4880, Hamamatsu Photonics K.K.). The cutoff filter was selected to fit the excitation wavelength of the compound. The exposure time was adjusted depending on the fluorescence intensity of each compound. Compound 2 as a test compound (0.5 mg/ml) was dissolved in physiological saline or phosphate buffer (pH7.4) and administered to the mice via a tail vein at the dose of 5.0 mg/Kg. At a given time after the administration of the test compound, the mice were anesthetized with diethyl ether and fluorescent light images of the entire body of the mice was photographed. For comparison, each of ICG (5 mg/kg, i.v.) and the following compound (Compound A) was administered and imaging was carried out in the same manner as above. The results are shown in FIGS. 1 to 3.

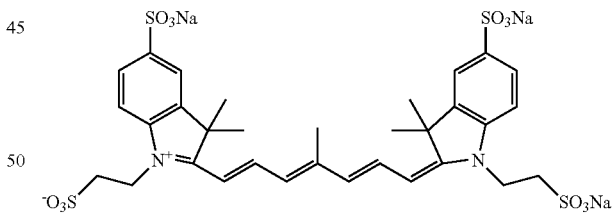

Compound 2 gave clear images of tumors at a shorter time after the administration as compared to the reference compounds. The position of tumor was not clear within 1 hour after the administration of the reference compounds. Whilst, Compound 2 successfully gave clear images of the tumor at 10 to 30 minutes after the administration and revealed to be highly effective as a fluorescent contrast agent (FIG. 1).

Test Example 2

Fluorescence Imaging Test

Tumor bearing mice were prepared in the same manner as Test Example 1, and conditions for irradiation was the same as those explained in Test Example 1. Compound 5, Compound 7, and Compound 10 were used as test compounds. Each of the test compounds (0.5 mg/ml) was dissolved in physiological saline or phosphate buffer (pH 7.4) and administered to the mice via a tail vein at the dose of 5.0 mg/Kg. For comparison, the following compound (Compound B, 5 mg/kg, i.v.) was administered to the mice.

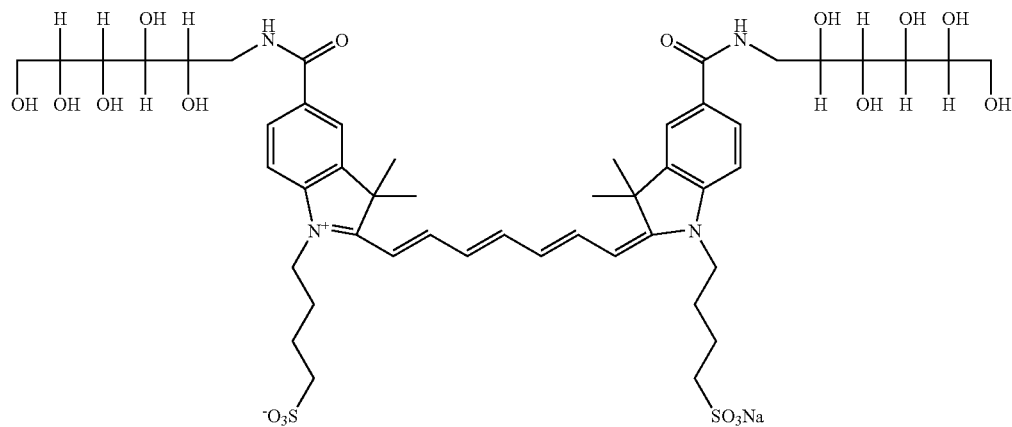

Figure 4:
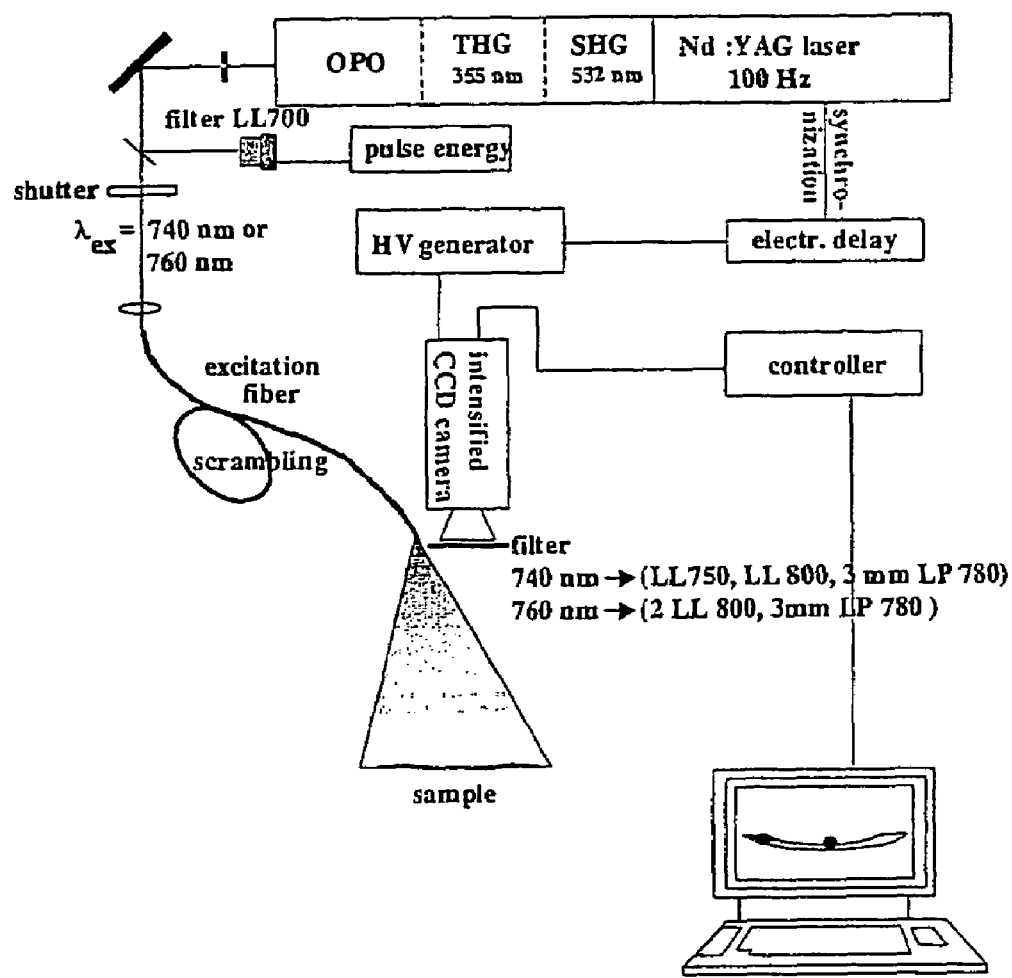
FIG. 4 is a schematic view of experimental set up for fluorescence imaging in Test Example 2. In the figure, SHG represents second harmonic generation; THG represents third harmonic generation; and OPO represents optical parametric oscillator.
Figure 5:
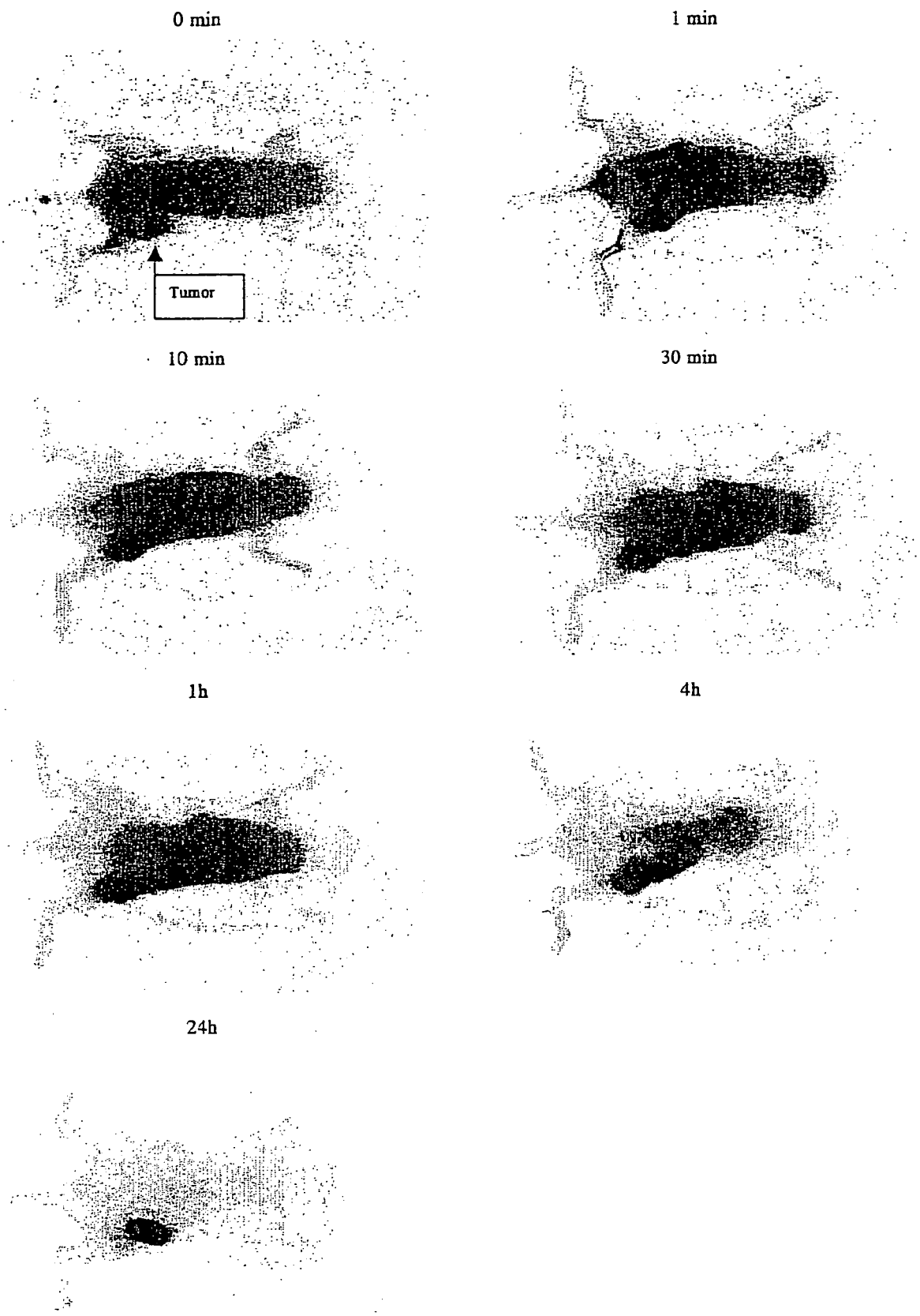
FIG. 5 is a photograph showing the results of fluorescence imaging at given times after the administration of Compound 5 of the present invention.
Figure 6:
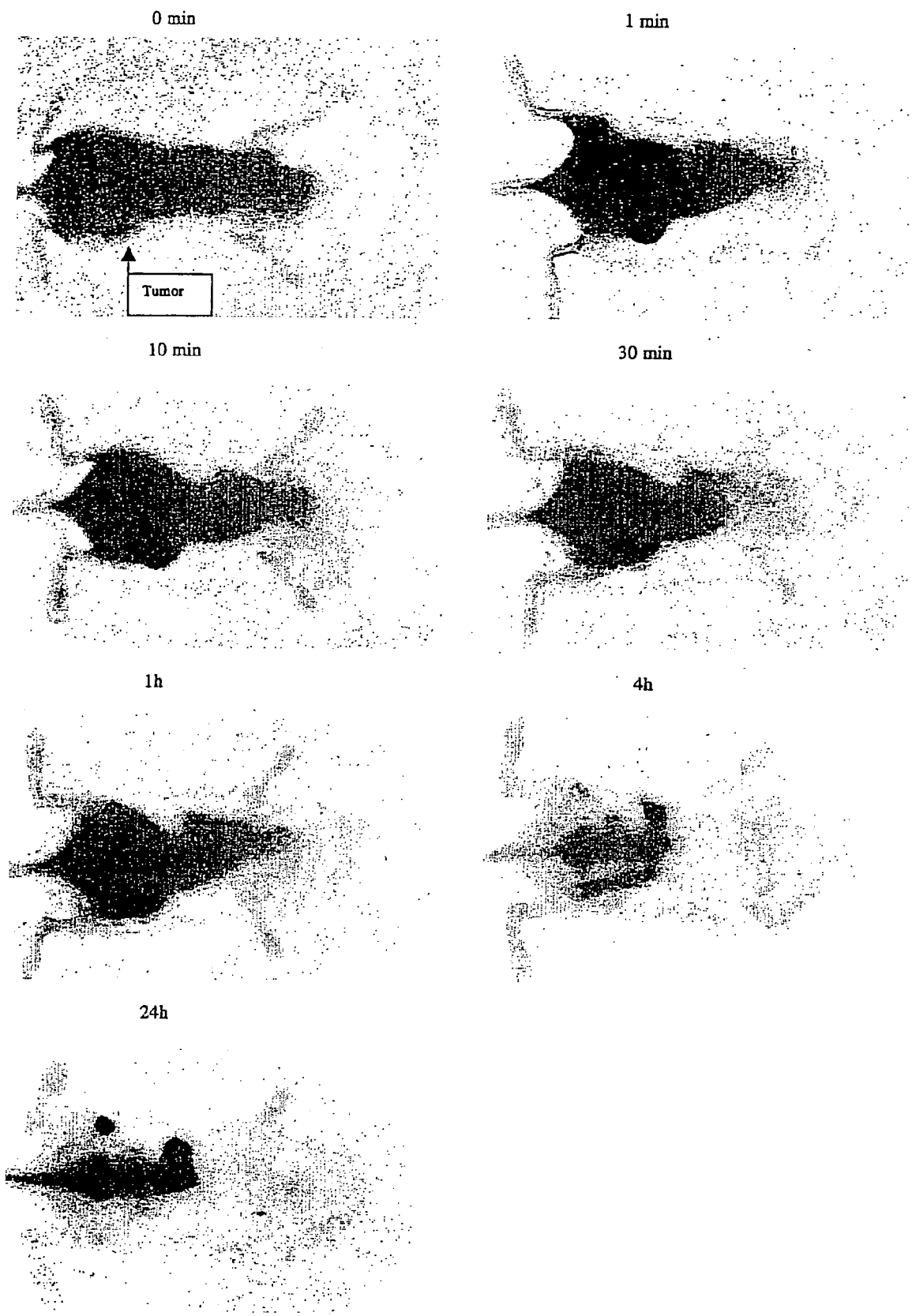
FIG. 6 is a photograph showing the results of fluorescence imaging at given times after the administration of Compound 7 of the present invention.
Figure 7:
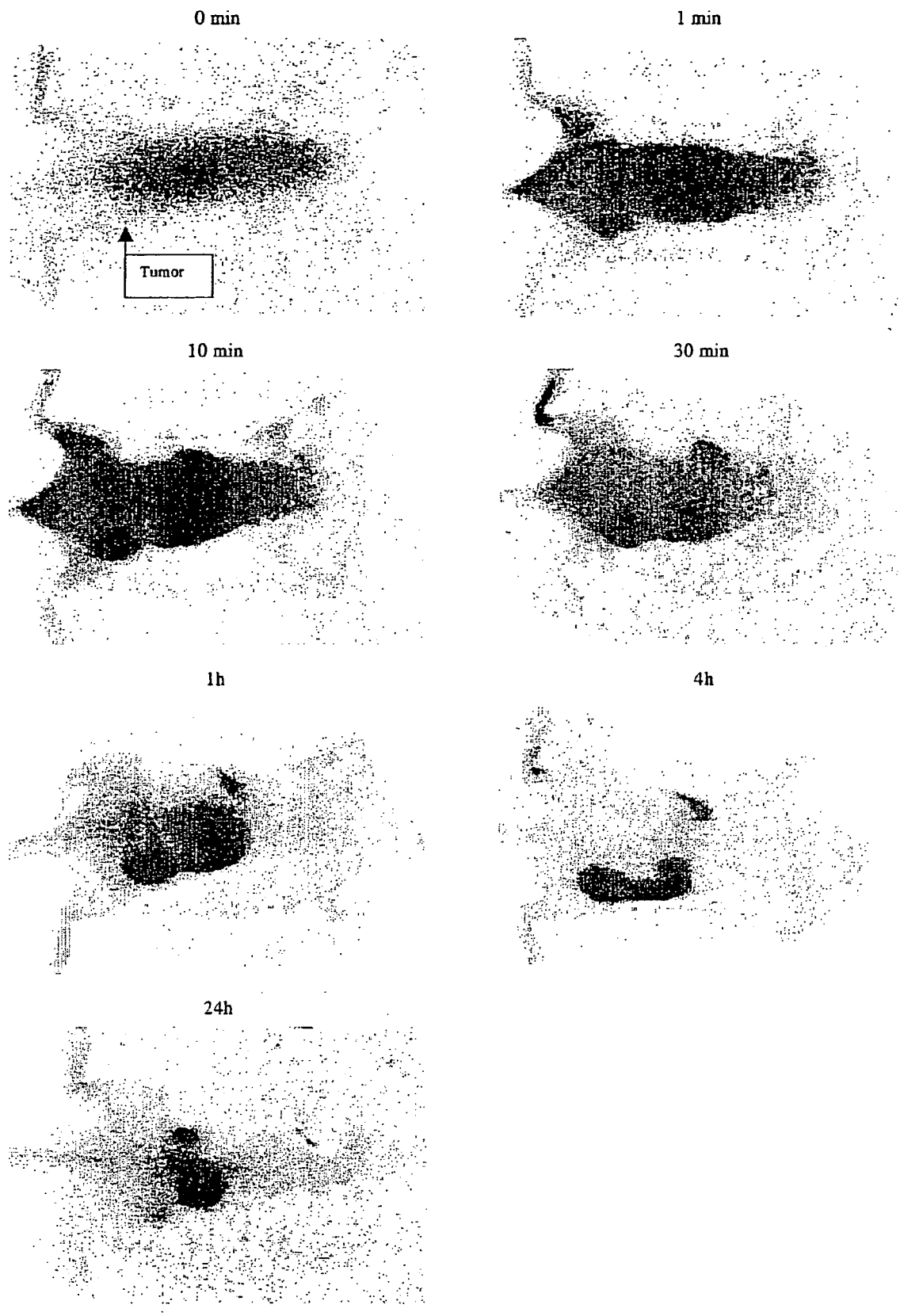
FIG. 7 is a photograph showing the results of fluorescence imaging at given times after the administration of Compound 10 of the present invention.
Figure 8:
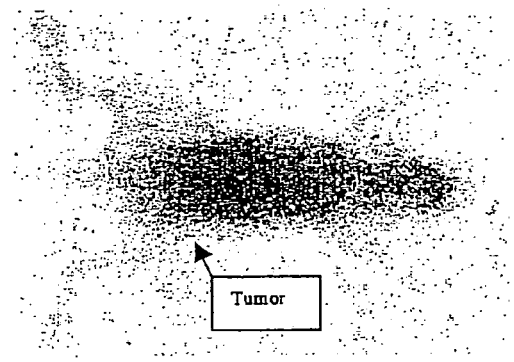
FIG. 8 is a photograph showing the results of fluorescence imaging at given times after the administration of Compound B as a reference.
Figure 8:
Figure 8:
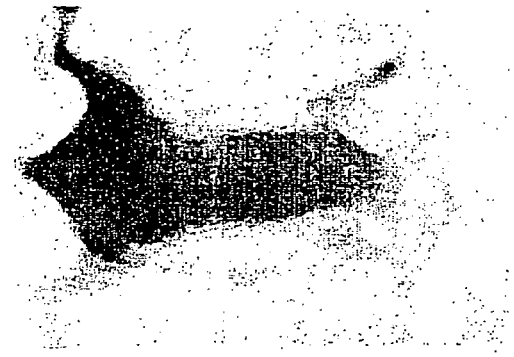
Figure 8:
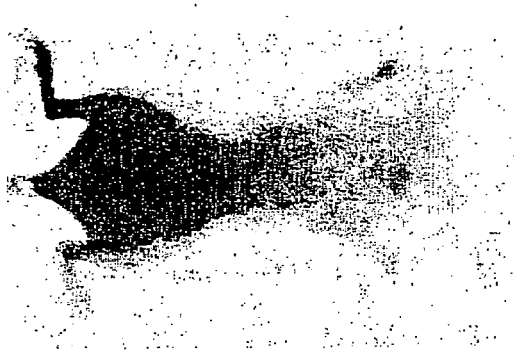
Figure 8:
Figure 8:
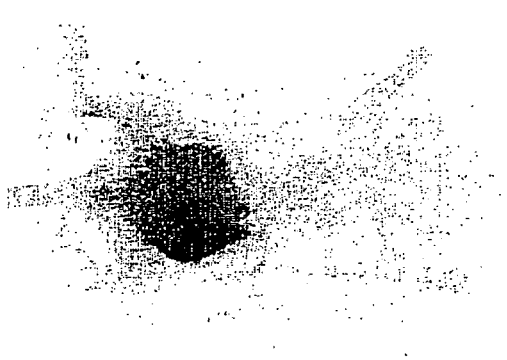
Figure 8:
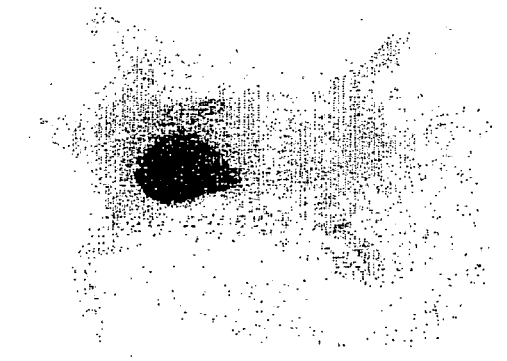

Light was generated using a tunable, pulsed, solid state laser system consisting of an optical parametric oscillator (OPO) pumped by the third harmonic of a Nd:Yag laser (Coherent Inc.). An excitation wavelength of λex=740 nm was chosen and guided with an optical fiber to the tumor bearing nude mice. The dye-specific fluorescence exitance was imaged using a filter combination (Corion) and an intensified CCD camera (Roper Scientific.) at different times after dye administration (FIG. 4). Fluorescence imagings were taken before administration, and 1 min, 10 min, 30 min, 60 min, 2 hours, 4 hours, 24 hours after intravenous dye administration via the lateral tail venous at a standard dose of 5 mg/kg. In the first 60 min, the body temperature of the animals was kept at 38° C. with heating pad. Fluorescence imaging properties of the compounds were compared in nude mice tumor models. The results are shown in FIGS. 5 to 8. Compound 5, Compound 7, and Compound 10 gave clear images of tumors at a shorter time after the administration as compared to the reference compound (Compound B). The position of tumor was not clear within 1 hour after the administration of the reference compound (FIG. 8). Whilst, the compounds of the present invention successfully gave clear images of the tumor at 10 to 30 minutes after the administration (FIGS. 5 to 7) and revealed to be highly effective as a fluorescent contrast agent

INDUSTRIAL APPLICABILITY

The near infrared fluorescence contrast agent of the present invention can emit near infrared fluorescence by an excitation light. The near infrared fluorescence is superior in permeability through biological tissues, and therefore, the agent enables the detection of a lesion in a deep part of a living body.

What is claimed is:

1. A method of fluorescence imaging, comprising introducing a near infrared fluorescent contrast agent comprising a compound of the formula below or a pharmaceutically acceptable salt thereof into a living body, exposing said body to an excitation light, and detecting near infrared fluorescence from the contrast agent

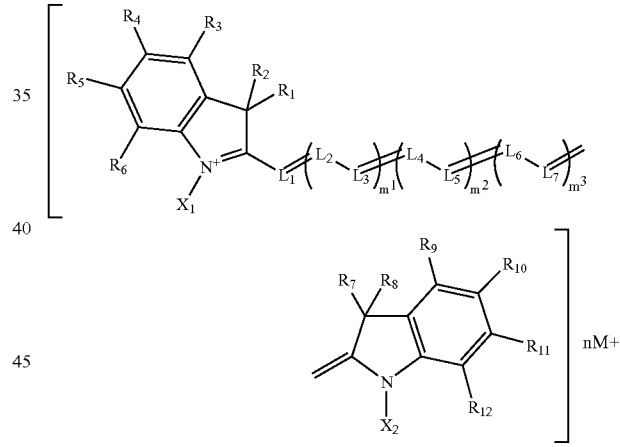

wherein $R^1, R^2, R^7$, and $R^8$ independently represent a substituted or unsubstituted $C_1$-$C_{10}$ alkyl group or a substituted or unsubstituted aryl group; or $R^1$ $R^2$ and/or $R^7$ and $R^8$ bind to each other to form a ring;

$R^3, R^4, R^5, R^6, R^9, R^{10}, R^{11}$ and $R^{12}$ independently represent a hydrogen atom, a substituted or unsubstituted $C_1$-$C_6$ alkyl group, a substituted or unsubstituted aryl group, a substituted or unsubstituted heteroaryl group, a halogen atom, cyano group, carboxyl group, or sulfo group; or two of $R^3, R^4, R^5, R^6, R^9, R^{10}, R^{11}$ and $R^{12}$ bind to each other to form a ring;

$X^2$ represent a substituted or unsubstituted $C_1$-$C_{15}$ alkyl group or a substituted or unsubstituted aryl group;

$X^1$ is a group represented by the following formula

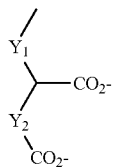

wherein $X^1$ and $X^2$ in total have 2 or 4 carboxyl groups;

$Y^1$ and $Y^2$ independently represent a substituted or unsubstituted divalent linking group;

$m^1$ represents 0 or 1;

$m^2$ represents 0 or 1;

$m^3$ represents 0 or 1;

$L^1$, $L^2$, $L^3$, $L^4$, $L^5$, $L^6$, and $L^7$ independently represent a substituted or unsubstituted methine group, provided that when two or more of the methine groups have substituents, the substituents bind to each other to form a ring;

M represents a hydrogen atom, a metal, or a quaternary ammonium salt; and n represents an integer of 1 to 7 necessary for neutralizing charge.

2. The method according to claim 1, wherein in the compound each of $m^1$, $m^2$, and $m^3$ is 1.

3. The method according to claim 1, wherein in the compound $X^1$ and $X^2$ independently represent a group represented by the following formula:

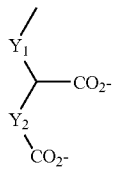

wherein $Y^1$ and $Y^2$ independently represent a substituted or unsubstituted divalent bond.

4. The method according to claim 1, wherein in the compound at least one of $R^3$, $R^4$, $R^5$, $R^6$, $R^9$, $R^{10}$, $R^{11}$, and $R^{12}$ is a substituted or unsubstituted aryl group or a substituted or unsubstituted heteroaryl group.

5. The method according to claim 1, wherein in the compound $Y_1$ represents —$(CH_2)_p$CONH—, p represents an integer of 1 to 4, and $Y_2$ represents —$(CH_2)$— or $(CH_2)_2$—.

6. The method according to claim 1 wherein the contrast agent is introduced into the living body and comprises a pharmaceutically acceptable carrier for diagnostic imaging.

7. The method of claim 6, which is for tumor imaging.

8. The method of claim 6, which is for angiography.

9. The method according to claim 6, wherein the pharmaceutically acceptable injectable carrier for diagnostic imaging is injectable distilled water.

10. The method according to claim 6, wherein the pharmaceutically acceptable injectable carrier for diagnostic imaging is physiological saline.

11. The method according to claim 6, wherein the pharmaceutically acceptable injectable carrier for diagnostic imaging is Ringer's solution.

12. The method according to claim 4, wherein in the compound at least one of $R^3$, $R^4$, $R^5$, $R^6$, $R^9$, $R^{10}$, $R^{11}$, and $R^{12}$ is a substituted or unsubstituted aryl group.

13. The method according to claim 4, wherein in the compound at least one of $R^3$, $R^4$, $R^5$, $R^6$, $R^9$, $R^{10}$, $R^{11}$, and $R^{12}$ is a substituted or unsubstituted heteroaryl group.

14. The method according to claim 1, wherein in the compound Y1 represents —$(CH_2)_p$CONH— and p represents an integer of 1 to 4.

15. The method to claim 1, wherein in the compound $Y_2$ represents —$(CH_2)$— or $(CH_2)_2$—.

16. The method of claim 1, which is for tumor imaging.

17. The method of claim 1, which is for angiography.

* * * * *

UNITED STATES PATENT AND TRADEMARK OFFICE
CERTIFICATE OF CORRECTION

PATENT NO. : 7,473,415 B2
APPLICATION NO. : 10/506819
DATED : January 6, 2009
INVENTOR(S) : Masayuki Kawakami Page 1 of 1

It is certified that error appears in the above-identified patent and that said Letters Patent is hereby corrected as shown below:

Column 44, line 55, reads "$R^1 R^2$" should read -- $R^1$ and $R^2$ --
Column 44, line 66, reads "$X^2$ represent" should read -- $X^2$ represents --
Column 45, lines 6, 10, 37, and 40, reads "$CO_2.$" should read -- $CO_2^-$ --
Column 46, line 12, reads "claim 1 wherein" should read -- claim 1, wherein --

Signed and Sealed this

Twenty-third Day of June, 2009

JOHN DOLL
*Acting Director of the United States Patent and Trademark Office*